United States Patent
Barbier et al.

(10) Patent No.: US 9,682,129 B2
(45) Date of Patent: Jun. 20, 2017

(54) TREATMENT OF COGNITIVE IMPAIRMENT OF HUNTER SYNDROME BY INTRATHECAL DELIVERY OF IDURONATE-2-SULFATASE

(71) Applicant: SHIRE HUMAN GENETIC THERAPIES, INC., Lexington, MA (US)

(72) Inventors: Ann Barbier, Lexington, MA (US); Thomas McCauley, Cambridge, MA (US); Charles W. Richard, III, Carlisle, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 14/367,864

(22) PCT Filed: Dec. 21, 2012

(86) PCT No.: PCT/US2012/071495
§ 371 (c)(1),
(2) Date: Jun. 20, 2014

(87) PCT Pub. No.: WO2013/096912
PCT Pub. Date: Jun. 27, 2013

(65) Prior Publication Data
US 2015/0328289 A1 Nov. 19, 2015

Related U.S. Application Data

(60) Provisional application No. 61/580,027, filed on Dec. 23, 2011, provisional application No. 61/590,797, filed on Jan. 25, 2012, provisional application No. 61/590,804, filed on Jan. 25, 2012, provisional application No. 61/609,173, filed on Mar. 9, 2012, provisional application No. 61/734,365, filed on Dec. 6, 2012.

(51) Int. Cl.
*C12N 9/48* (2006.01)
*A61K 38/46* (2006.01)
*A61K 9/00* (2006.01)
*C12N 9/16* (2006.01)

(52) U.S. Cl.
CPC .......... *A61K 38/465* (2013.01); *A61K 9/0019* (2013.01); *A61K 9/0085* (2013.01); *A61K 38/46* (2013.01); *C12N 9/16* (2013.01); *C12Y 301/06013* (2013.01)

(58) Field of Classification Search
CPC .... C12Y 301/06013; C12N 9/48; A61K 9/85; A61K 38/46
See application file for complete search history.

(56) References Cited

U.S. PATENT DOCUMENTS

| 8,545,837 | B2 * | 10/2013 | Zhu ....................... A61K 9/0085 424/94.3 |
| 8,926,967 | B2 * | 1/2015 | Dodge ................. A61K 38/465 424/94.6 |
| 9,220,677 | B2 * | 12/2015 | Zhu ....................... A61K 9/0085 |
| 2005/0048047 | A1 | 3/2005 | Kakkis et al. |
| 2009/0130079 | A1 | 5/2009 | Dodge et al. |
| 2010/0068183 | A1 | 3/2010 | Whitley et al. |
| 2010/0068195 | A1 | 3/2010 | Vellard et al. |
| 2011/0318323 | A1 | 12/2011 | Zhu et al. |

FOREIGN PATENT DOCUMENTS

| WO | WO-2011/163648 A1 | 12/2011 |
| WO | WO-2011/163649 A2 | 12/2011 |

OTHER PUBLICATIONS

Fan et al. 2010; Correlation of automated volumetric analysis of brain MR imaging with cognitive impairment in natural history study of mucopolysaccharidosis II. Am J Neuroradiol. 31: 1319-1323.*
Peters et al. 1996; Outcome of unrelated donor bone marrow transplantation in 40 children with Hurler Syndrome. Blood. 87(11): 4894-4902.*
International Search Report for PCT/US12/71495 mailed Apr. 5, 2013.
Written Opinion for PCT/US12/71495 mailed Apr. 5, 2013.
Calias et al: "CNS Penetration of Intrathecal—Lumbar Idursulfase in the Monkey, Dog and Mouse : Implications for Neurological Outcomes of Lysosomal Storage Disorder"; PLOS ONE, vol. 7; No. 1, Jan. 18, 2012 (Jan. 18, 2012 ).
Felice et al: "Safety Evaluation of 1-14 Chronic Intrathecal Administration of Idursulfase-IT in Cynomolgus Monkeys"; Toxicologic Pathology, vol . 39, No. 5, May 31, 2011 (May 31, 2011) , pp. 879-892.

* cited by examiner

*Primary Examiner* — Karen Cochrane Carlson
(74) *Attorney, Agent, or Firm* — Fangli Chen; Emily E. Bates; Proskauer Rose LLP

(57) ABSTRACT

The present invention provides a method of treating cognitive impairment of Hunter syndrome. Among other things, the present invention provides a method comprising a step of administering intrathecally to a subject in need of treatment a recombinant iduronate-2-sulfatase (I2S) enzyme at a therapeutically effective dose and an administration interval for a treatment period sufficient to improve, stabilize or reduce declining of one or more cognitive, adaptive, motor, and/or executive functions relative to a control.

29 Claims, 21 Drawing Sheets

Final Linked Structural Models for I2S in Serum and CSF

Allometrically Scaled PopPK Parameters to Pediatrics for IT-I2S After Correction for Brain/BW Ratio Difference Between NHP & Children

| Matrix | Parameters | Estimates in Monkey | Scaling Factor[a] [BWhuman/BWnhp][b] | Estimated Parameters in Children (<6 y. old) (Typical 10 kg) | Estimated Parameters in Juveniles (6-17 y.old) (Typical 50 kg) |
|---|---|---|---|---|---|
| Serum | $V_c$ (mL) | 99.2 | 3.66 or 18.3 | 363 | 1817 |
| | $V_p$ (mL) | 310 | 3.66 or 18.3 | 1136 | 5678 |
| | CL (mL/h) | 149 | 2.65 or 8.85 | 395 | 1319 |
| | CLd (mL/h) | 90.4 | 2.65 or 8.85 | 239 | 800 |
| CSF | $V_{CSF}$ (mL) | 1.15 | 3.66 or 18.3 | 4 | 21 |
| | $V_2$ (mL) | 6.31 | 3.66 or 18.3 | 23 | 116 |
| | $V_3$ (mL) | 2.27 | 3.66 or 18.3 | 8 | 42 |
| | $CL_{CSF}$ (mL/h) | 0.224 | 2.65 or 8.85 | 1 | 2 |
| | $CL_2$ (mL/h) | 0.455 | 2.65 or 8.85 | 1 | 4 |
| | $CL_3$ (mL/h) | 1.60 | 2.65 or 8.85 | 4 | 14 |
| | $K_{IN}$ (1/h) | 0.273 | 0.723 or 0.483 | 0.197 | 0.132 |
| | F(%) (SYS to CSF) | 0.0492 | NA | 0.0492 | 0.0492 |
| | $K_{OUT}$ (1/h) | 0.124 | 0.723 or 0.483 | Kout*R = 0.043 | 0.0599 |
| | Lag (h) | 0.0665 | NA | 0.0665 | 0.0665 |
| | F(%) (CSF to SYS) | 51.1 | NA | F*R = 10.7 | 51.1 |

[a] Using BW of 2.73 kg in Monkeys and corresponding BW in man. [b] = 0.75 for clearances, 1 for volumes and -0.25 for rates, R = 0.209, Brain /Body Weight Ratio Monkey over Child

Fig. 5

Predicted profile after IV administration well-predicted by scaled NC model

SEQUENCE LISTING

<160> NUMBER OF SEQ ID NOS: 2

<210> SEQ ID NO 1
<211> LENGTH: 525
<212> TYPE: PRT
<213> ORGANISM: Homo sapiens

<400> SEQUENCE: 1

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

```
Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525

<210> SEQ ID NO 2
<211> LENGTH: 550
<212> TYPE: PRT
<213> ORGANISM: Homo sapiens

<400> SEQUENCE: 2

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
210                 215                 220
```

```
Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
        355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
        435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
        515                 520                 525

Pro Leu Gln Asp His Asn Met Tyr Asn Asp Ser Gln Gly Gly Asp Leu
    530                 535                 540

Phe Gln Leu Leu Met Pro
545                 550
```

TREATMENT OF COGNITIVE IMPAIRMENT OF HUNTER SYNDROME BY INTRATHECAL DELIVERY OF IDURONATE-2-SULFATASE

RELATED APPLICATIONS

This application claims the benefit of U.S. Provisional Application No. 61/580,027, filed on Dec. 23, 2011; U.S. Provisional Application No. 61/590,797, filed on Jan. 25, 2012; U.S. Provisional Application No. 61/590,804, filed on Jan. 25, 2012; U.S. Provisional Application No. 61/609,173, filed on Mar. 9, 2012; U.S. Provisional Application No. 61/734,365, filed on Dec. 6, 2012; the disclosures of each of which are incorporated herein by reference.

BACKGROUND

Hunter syndrome, also known as mucopolysaccharidosis Type II (MPS II), is a lysosomal storage disease caused by deficiency or absence of enzyme, iduronate-2-sulfatase (I2S). Iduronate-2-sulfatase is involved in break down and recycle of specific mucopolysaccharides, also known as glycosaminoglycans or GAG. As a result, in Hunter syndrome, GAG builds up in cells throughout the body, which interferes with the normal function of various cells and organs in the body, resulting in a number of serious symptoms. In many cases of Hunter syndrome, there is often a large build-up of GAGs in neurons and meninges of affected individuals, leading to various forms of CNS symptoms, impaired cognitive performance and developmental delays.

Enzyme replacement therapy (ERT) has been used to treat Hunter syndrome. Approved therapy uses intravenous administration of recombinant I2S enzyme. However, intravenously administered enzyme typically does not adequately cross the blood-brain barrier (BBB) into the cells and tissues of the CNS. Therefore, treatment of CNS symptoms of Hunter syndrome has been especially challenging.

SUMMARY

The present invention provides an effective method for treating Hunter syndrome, in particular, Hunter syndrome with cognitive impairment based on intrathecal administration of recombinant iduronate-2-sulfatase (I2S) enzyme. The present invention is, in part, based on the first-in-human clinical study demonstrating safety, tolerability and efficacy of intrathecal delivery of I2S enzyme in Hunter syndrome (MPS II) patients (e.g., from 3-12 years old) with evidence of cognitive impairment. For example, as described in the Examples section below, intrathecal administration of recombinant I2S enzyme was safe, well tolerated and resulted in significant reduction of GAG levels in cerebrospinal fluid (CSF) of the patients in all dose groups including IT dose as low as 1 mg per dose. In many cases, the decline of GAG in CSF was evident after the first IT dose of I2S enzyme. Since the GAG level in CSF is an important indicator of pharmacodynamic activity of I2S in the intrathecal compartment, these results demonstrate that intrathecally administered I2S has unexpectedly superior pharmacodynamics activity in the CNS. Consistent with this observation, intrathecally administered I2S also resulted in stabilization or improvements in cognitive performance, including neurocognitive, adaptive and/or executive functions, in several patients after receiving only 6 months of treatment with intrathecal administration of US enzyme. This first-in-human clinical study confirms that intrathecal delivery of recombinant I2S enzyme is a safe and effective method for treating Hunter syndrome. In particular, the cognitive data from this first-in-human clinical trial demonstrate that intrathecal delivery of MS enzyme may be used to effectively treat CNS symptoms of Hunter syndrome, resulting in stabilization or improvement of cognitive performance. It is contemplated that longer duration of treatment in patients who begin intrathecal therapy early in the trajectory of neurodevelopmental decline may be particularly effective in treating cognitive impairment.

Thus, in one aspect, the present invention provides a method of treating Hunters Syndrome comprising a step of administering intrathecally to a subject in need of treatment a recombinant iduronate-2-sulfatase (I2S) enzyme at a therapeutically effective dose and an administration interval such that one or more cognitive or developmental abilities are improved relative to a control. In some embodiments, the present invention provides a method of treating Hunter syndrome comprising a step of administering intrathecally to a subject in need of treatment a recombinant iduronate-2-sulfatase (I2S) enzyme at a therapeutically effective dose and an administration interval for a treatment period sufficient to improve, stabilize or reduce declining of one or more cognitive, adaptive, motor, and/or executive functions relative to a control. As used herein, the terms "improve," "stabilize" or "reduce," or grammatical equivalents, indicate an assessment or measurement of cognitive, adaptive, motor, and/or executive functions (e.g., cognitive test scores) that are relative to a baseline assessment or measurement, such as an assessment or measurement in the same individual prior to initiation of the treatment, or an assessment or measurement in a control individual (or multiple control individuals) in the absence of the treatment. A "control individual" is an individual afflicted with Hunter syndrome as the individual being treated, who is about the same age as the individual being treated (to ensure that the stages of the disease, as well as the stage of childhood development, in the treated individual and the control individual(s) are comparable).

In some embodiments, a therapeutically effective dose is or greater than about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg. In particular embodiments, a therapeutically effective dose is or greater than about 10 mg. In particular embodiments, a therapeutically effective dose is or greater than about 30 mg. In some embodiments, a therapeutically effective dose is less than about 50 mg, 45 mg, 40 mg, 35 mg, 30 mg, 25 mg, 20 mg, 15 mg, or 10 mg. In particular embodiments, a therapeutically effective dose is less than about 30 mg. In some embodiments, a therapeutically effective dose ranges between about 1-100 mg, about 5-100 mg, about 5-90 mg, about 5-80 mg, about 5-70 mg, about 5-60 mg, about 5-60 mg, about 10-100 mg, about 10-90 mg, about 10-80 mg, about 10-70 mg, about 10-60 mg, or about 10-50 mg.

In some embodiments, a suitable therapeutically effective dose, once administered regularly at the administration interval, results in serum $AUC_{ss}$ of the recombinant I2S enzyme within a range from approximately 200,000 min·ng/mL to approximately 1,000,000 min·ng/mL (e.g., from approximately 250,000 min·ng/mL to approximately 900,000 min·ng/mL, from approximately 300,000 min·ng/mL to approximately 800,000 min·ng/mL, from approximately 350,000 min·ng/mL to approximately 700,000 min·ng/mL, from approximately 400,000 min·ng/mL to approximately 600,000 min·ng/mL).

In some embodiments, a suitable therapeutically effective dose, once administered regularly at the administration interval, results in maximum serum concentration ($C_{max}$) of the recombinant I2S enzyme within a range from approximately 60 to approximately 300 ng/mL (e.g., from approximately 70 to approximately 250 ng/mL, from approximately 70 to approximately 200 ng/mL, from approximately 70 to approximately 150 ng/mL, from approximately 80 to approximately 250 ng/mL, from approximately 80 to approximately 200 ng/mL, from approximately 80 to approximately 150 ng/mL, from approximately 90 to approximately 250 ng/mL, from approximately 90 to approximately 200 ng/mL, from approximately 90 to approximately 150 ng/mL).

In some embodiments, suitable administration interval is weekly, once every two weeks, twice a month, once every three weeks, monthly, once every two months, once every three months, once every four months, once every five months, once every six months, twice a year, once a year, or at a variable interval. As used herein, monthly is equivalent of once every four weeks.

In some embodiments, intrathecal administration is through lumbar puncture. In some embodiments, intrathecal administration is through an Ommaya reservoir. In some embodiments, intrathecal administration is through intermittent or continuous access to an implanted intrathecal drug delivery device (IDDD). In some embodiments, intrathecal administration is through continuous access to an implanted IDDD for, e.g., greater than 0.1, 0.2, 0.3, 0.4, 0.5, 1.0, 1.5, 2.0, 2.5, 3.0, 3.5, 4.0, 4.5, or 5.0 hours.

In some embodiments, a treatment period is at least 1, 2, 3, 4, 5, 6, 8, 10, 12, 18, 24, or more months. In some embodiments, a treatment period is at least 1, 2, 3, 4, 5, 6, 7, 8, 9, 10 years or longer. In some embodiments, a treatment period is the life-time of the subject being treated.

In some embodiments, the one or more cognitive, adaptive, motor, and/or executive functions are assessed by the Differential Ability Scales—Second Edition (DAS-II). In some embodiments, the DAS-II assessment is by a raw score, cluster score, standardized score, percentile age equivalent, or developmental quotient. In some embodiments, the DAS-II assessment is by a general conceptual ability (GCA) score. In some embodiments, the one or more cognitive, adaptive, motor, and/or executive functions are assessed by Bayley Scales of Infant Development Version III (BSID-III).

In some embodiments, intrathecal administration of the recombinant I2S enzyme results in improved GCA score or BSID-III developmental quotient (DQ) relative to a control (e.g., baseline pre-treatment score). In some embodiments, intrathecal administration of the recombinant I2S enzyme improves the GCA score or BSID-III developmental quotient by about 5, 10, 11, 12, 13, 14, 15, 20, 25, 30 points or more as compared to a control (e.g., baseline pre-treatment score). In some embodiments, intrathecal administration of the recombinant I2S enzyme improves the GCA score or BSID-III developmental quotient by about 10%, 15%, 20%, 25%, 30%, 35%, 40%, 45%, 50% or more as compared to a control (e.g., baseline pre-treatment score). In some embodiments, the improved GCA score or BSID-III developmental quotient is within the range of 85-105 within the range of approximately 70-105 (e.g., approximately 75-105, 75-100, 70-100, 70-95, 70-90, 75-105, 75-100, 75-95, 75-90, 80-105, 80-100, 80-95, 80-90, 85-105, 85-100, or 85-95). In some embodiments, the improved GCA score or BSID-III developmental quotient is or greater than about 70, 75, 80, 85, 86, 87, 88, 89, 90, 95, 96, 97, 98, 99, 100, 101, 102, 103, 104, or 105 points. In some embodiments, the GCA score or BSID-III developmental quotient is measured after a treatment period of or longer than 3, 4, 5, 6, 7, 8, 9, 10, 11, 12, or 18 months. In some embodiments, intrathecal administration of the recombinant I2S enzyme maintains the improved GCA score or BSID-III developmental quotient for a period of or longer than 3, 6, 9, 12, 15, 18, 21, 24, 27, 30, 33, or 36 months. As used herein, maintaining the GCA score or BSID-III developmental quotient means the change of GCA score or BSID-III developmental quotient is less than 10, 9, 8, 7, 6, or 5 points within a period of 3, 6, 8, 10, 12 months or the change of the GCA score or BSID-III developmental quotient over a period of 3, 6, 8, 10, 12 months is within 20%, 15%, 10%, 5% of the mean over such period.

In some embodiments, intrathecal administration of the recombinant I2S enzyme results in stabilization of the GCA score or BSID-III developmental quotient relative to a control (e.g., baseline pre-treatment score). In some embodiments, intrathecal administration of the recombinant I2S enzyme results in stabilization of the GCA score or BSID-III developmental quotient relative to the baseline pre-treatment score after a treatment period of or longer than 3, 4, 5, 6, 7, 8, 9, 10, 11, 12, 18 months, or 1, 2, 3, 4, 5, 10 years. As used herein, stabilization of the GCA score or BSID-III developmental quotient means the change of GCA score or BSID-III developmental quotient from the baseline is less than 10, 9, 8, 7, 6, or 5 points within 3, 6, 8, 10, 12 months or the change of the GCA score or BSID-Ill developmental quotient over a period of 3, 6, 8, 10, 12 months within 20%, 15%, 10%, 5% of the mean over such period. In some cases, stabilization of the GCA score or BSID-III developmental quotient means the change of GCA score or BSID-III developmental quotient from the baseline is less than 20%, 15%, 10%, 5% within 3, 6, 8, 10, 12 months. In some embodiments, intrathecal administration of the recombinant I2S enzyme results in stabilization of the GCA score or BSID-III developmental quotient following the initial declining of the GCA score or BSID-III developmental quotient. For example, stabilization may follow after no less than 40%, 35%, 30%, 25%, 20%, 15%, or 10% declining of the GCA score or BSID-III developmental quotient from the baseline. In some embodiments, intrathecal administration of the recombinant I2S enzyme stabilizes the GCA score or BSID-III developmental quotient for a period of or longer than 3, 6, 9, 12, 15, 18, 21, 24, 27, 30, 33, or 36 months. In some embodiments, intrathecal administration of the recombinant I2S enzyme stabilizes the GCA score or BSID-III developmental quotient for a period of 3-36 months (e.g., 3-33, 3-30, 3-27, 3-24, 3-21, 3-18, 3-15, 3-12, 3-9, 3-6, 6-36, 6-33, 6-30, 6-27, 6-24, 6-21, 6-18, 6-15, 6-12, 6-9 months).

In some embodiments, intrathecal administration of the recombinant I2S enzyme results in reduced declining of the GCA score or BSID-III developmental quotient. In some embodiments, intrathecal administration of the recombinant US enzyme results in the annual decline of the GCA score or BSID-III developmental quotient less than about 20, 19, 18, 17, 16, 15, 14, 13, 12, 11, or 10 points. In some embodiments, intrathecal administration of the recombinant I2S enzyme results in the annual decline of the GCA score or BSID-III developmental quotient less than about 40%, 35%, 30%, 25%, 20%, 15%, or 10%. In some embodiments, reduced declining of the GCA score or BSID-III developmental quotient is achieved after a treatment period of or longer than 3, 4, 5, 6, 7, 8, 9, 10, 11, 12, 18 months, or 1, 2, 3, 4, 5, 10 years.

In some embodiments, intrathecal administration of the recombinant I2S enzyme further results in improvement or stabilization of one or more adaptive functions assessed by the Scales of Independent Behavior-Revised (SIB-R). In some embodiments, intrathecal administration of the recombinant I2S enzyme further results in improvement or stabilization of one or more executive functions assessed by the Behavior Rating Inventory of Executive Function® (BRIEF®).

The present invention may be used to treat a subject of various ages. In some embodiments, a subject being treated is at least 6 moths old, 12 months old, at least 18 months old, 2 years old, 2.5 years old, 3 years old, 3.5 years old, 4 years old, 4.5 years old, or 5 years old. In some embodiments, a subject being treated is younger than 5, 4.5, 4, 3.5, 3, 2.5, 2, or 1.5 years old. In some embodiments, a subject being treated is younger than 12, 11, 10, 9, 8, 7, 6, 5, 4, 3, 2 or 1 month old. In some embodiments, a subject being treated is younger than 29, 28, 27, 26, 25, 24, 23, 22, 21, 20, 19, 18, 17, 16, 15, 14, 13, 12, 11, 10, 9, 8, 7, 6, 5, 4, 3, 2, 1 day(s) old. In some embodiments, a subject being treated is within the age range of 0 months-8 years, 3 months-8 years, 6 months-8 years, 8 months-8 years, 1 year-8 years, 3 months-7 years, 6 months-7 years, 8 months-7 years, 1 year-7 years, 3 months-6 years, 6 months-6 years, 8 months-6 years, 1 year-6 years, 3 months-5 years, 6 months-5 years, 8 months-5 years, 1 year-5 years, 3 months-4 years, 6 months-4 years, 8 months-4 years, 1 year-4 years, 3 months-3 years, 6 months-3 years, 8 months-3 years, 1 year-3 years, 3 months-2 years, 6 months-2 years, 8 months-2 years, or 1 year-2 years, 3 months-1 year, 6 months-1 year, or 8 months-1 year old.

In some embodiments, a subject being treated has cognitive impairment. In some embodiments, a subject being treated has a GCA score or BSID-III developmental quotient less than 100, 90, 80, 70, 60, 50, 40, 30, 20, 15, 10 or not testable before the treatment. In some embodiments, a subject being treated has a GCA score or BSID-III developmental quotient declined from normal baseline less than about 40%, 35%, 30%, 25%, 20%, 15%, or 10% before the treatment. In some embodiments, a subject being treated has a GCA score or BSID-III developmental quotient ranging between about 60-100 (e.g., about 60-95, 60-90, 60-85, 60-80, 60-75, 60-70, 70-100, 70-95, 70-90, 70-85, 70-80, 80-100, 80-95, 80-90) before the treatment.

In various embodiments, intrathecal administration is performed in conjunction with intravenous administration of the recombinant I2S enzyme. In some embodiments, intravenous administration of the recombinant I2S enzyme is weekly. In some embodiments, the intravenous administration of the recombinant I2S enzyme is weekly except the week when the intrathecal administration is performed. In some embodiments, the intravenous administration of the recombinant I2S enzyme is biweekly, once every three weeks, monthly, twice a month, once every two, three, four, five, or six months. In some embodiments, the intravenous administration of the recombinant I2S enzyme is at a dose of about 0.1, 0.2, 0.3, 0.4, 0.5, 0.6, 0.7, 0.8, 0.9, or 1.0 mg/kg body weight. In some embodiments, the intravenous administration of the recombinant I2S enzyme is at a dose of about 0.5 mg/kg body weight.

In some embodiments, the dose and/or administration interval for intrathecal and/or intravenous administration may be adjusted (e.g., increasing or decreasing) based on the GCA, BSID-III, SIB-R, and/or BRIEF score.

In various embodiments, intrathecal administration according to the invention results in no serious adverse effects in the subject. In various embodiments, intrathecal administration according to the invention does not require an immunosuppressant.

In particular embodiments, the present invention provides a method of treating Hunter syndrome comprising administering intrathecally to a subject in need of treatment a recombinant iduronate-2-sulfatase (I2S) enzyme at a first therapeutically effective dose and administering intravenously to the subject the recombinant I2S enzyme at a second therapeutically effective dose for a treatment period sufficient to improve, stabilize or reduce declining of one or more cognitive, adaptive, motor, and/or executive functions relative to a control. In some embodiments, the intrathecal administration is monthly. In some embodiments, the intravenous administration is weekly.

In another aspect, the present invention provides a method of treating Hunter syndrome comprising a step of administering intrathecally to a subject in need of treatment a recombinant iduronate-2-sulfatase (I2S) enzyme at a therapeutically effective dose and an administration interval for a treatment period sufficient to decrease glycosaminoglycan (GAG) level in the cerebrospinal fluid (CSF) relative to a control. As used herein, the term "decrease," or equivalent such as "reduce," or grammatical equivalents, indicate a measurement of GAG level that is relative to a baseline measurement, such as a measurement in the same individual prior to initiation of the treatment, or a measurement in a control individual (or multiple control individuals) in the absence of the treatment. A "control individual" is an individual afflicted with Hunter syndrome as the individual being treated, who is about the same age as the individual being treated (to ensure that the stages of the disease in the treated individual and the control individual(s) are comparable).

In some embodiments, a therapeutically effective dose is or greater than about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg. In particular embodiments, a therapeutically effective dose is or greater than about 10 mg. In particular embodiments, a therapeutically effective dose is or greater than about 30 mg. In some embodiments, a therapeutically effective dose is less than about 50 mg, 45 mg, 40 mg, 35 mg, 30 mg, 25 mg, 20 mg, 15 mg, or 10 mg. In particular embodiments, a therapeutically effective dose is less than about 30 mg. In some embodiments, a therapeutically effective dose ranges between about 1-100 mg, about 5-100 mg, about 5-90 mg, about 5-80 mg, about 5-70 mg, about 5-60 mg, about 5-60 mg, about 10-100 mg, about 10-90 mg, about 10-80 mg, about 10-70 mg, about 10-60 mg, or about 10-50 mg.

In some embodiments, a suitable therapeutically effective dose, once administered regularly at the administration interval, results in serum $AUC_{ss}$ of the recombinant I2S enzyme within a range from approximately 200,000 min·ng/mL to approximately 1,000,000 min·ng/mL (e.g., from approximately 250,000 min·ng/mL to approximately 900,000 min·ng/mL, from approximately 300,000 min·ng/mL to approximately 800,000 min·ng/mL, from approximately 350,000 min·ng/mL to approximately 700,000 min·ng/mL, from approximately 400,000 min·ng/mL to approximately 600,000 min·ng/mL).

In some embodiments, a suitable therapeutically effective dose, once administered regularly at the administration interval, results in maximum serum concentration ($C_{max}$) of the recombinant I2S enzyme within a range from approximately 60 to approximately 300 ng/mL (e.g., from approximately 70 to approximately 250 ng/mL, from approximately 70 to approximately 200 ng/mL, from approximately 70 to approximately 150 ng/mL, from approximately 80 to approximately 250 ng/mL, from approximately 80 to approximately 200 ng/mL, from approximately 80 to approximately 150 ng/mL, from approximately 90 to approximately 250 ng/mL, from approximately 90 to approximately 200 ng/mL, from approximately 90 to approximately 150 ng/mL).

In some embodiments, suitable administration interval is weekly, once every two weeks, twice a month, once every three weeks, monthly, once every two months, once every three months, once every four months, once every five months, once every six months, twice a year, once a year, or at a variable interval. As used herein, monthly is equivalent of once every four weeks.

In some embodiments, intrathecal administration is through lumbar puncture. In some embodiments, intrathecal administration is through an Ommaya reservoir. In some embodiments, intrathecal administration is through intermittent or continuous access to an implanted intrathecal drug delivery device (IDDD). In some embodiments, intrathecal administration is through continuous access to an implanted IDDD for, e.g., greater than 0.1, 0.2, 0.3, 0.4, 0.5, 1.0, 1.5, 2.0, 2.5, 3.0, 3.5, 4.0, 4.5, or 5.0 hours.

In some embodiments, a treatment period is at least 1, 2, 3, 4, 5, 6, 8, 10, 12, 18, 24, or more months. In some embodiments, a treatment period is at least 1, 2, 3, 4, 5, 6, 7, 8, 9, 10 years or longer. In some embodiments, a treatment period is the life-time of the subject being treated.

In some embodiments, intrathecal administration of the recombinant I2S enzyme results in the GAG level in the CSF lower than about 1000 ng/ml (e.g., lower than about 900 ng/ml, 800 ng/ml, 700 ng/ml, 600 ng/ml, 500 ng/ml, 400 ng/ml, 300 ng/ml, 200 ng/ml, 100 ng/ml, 50 ng/ml, 10 ng/ml, or 1 ng/ml).

In some embodiments, a subject being treated is at least 6 months old, 12 months old, 18 months old, 2 years old, 2.5 years old, 3 years old, 3.5 years old, 4 years old, 4.5 years old, or 5 years old. In some embodiments, a subject being treated is younger than 5, 4.5, 4, 3.5, 3, 2.5, 2, or 1.5 years old. In some embodiments, a subject being treated is younger than 12, 11, 10, 9, 8, 7, 6, 5, 4, 3, 2 or 1 month old. In some embodiments, a subject being treated is younger than 29, 28, 27, 26, 25, 24, 23, 22, 21, 20, 19, 18, 17, 16, 15, 14, 13, 12, 11, 10, 9, 8, 7, 6, 5, 4, 3, 2, 1 day(s) old. In some embodiments, the subject in need of treatment has a GAG level in the CSF greater than about 300, 400, 500, 600, 700, 800, 900, 1000, 1500, or 2000 ng/ml before the treatment.

In various embodiments, intrathecal administration is performed in conjunction with intravenous administration of the recombinant I2S enzyme. In some embodiments, intravenous administration of the recombinant I2S enzyme is weekly. In some embodiments, the intravenous administration of the recombinant I2S enzyme is weekly except the week when the intrathecal administration is performed. In some embodiments, the intravenous administration of the recombinant I2S enzyme is biweekly, once every three weeks, monthly, twice a month, once every two, three, four, five, or six months. In some embodiments, the intravenous administration of the recombinant I2S enzyme is at a dose of about 0.1, 0.2, 0.3, 0.4, 0.5, 0.6, 0.7, 0.8, 0.9, or 1.0 mg/kg body weight. In some embodiments, the intravenous administration of the recombinant I2S enzyme is at a dose of about 0.5 mg/kg body weight.

In various embodiments, a method according to the present invention further comprises a step of adjusting the dose and/or administration interval for intrathecal and/or intravenous administration based on the GAG level in the CSF. In some embodiments, the step of adjusting comprises increasing the therapeutic effective dose for intrathecal administration if the GAG level in the CSF fails to decrease relative to the control after 6, 5, 4, or 3 doses. In some embodiments, the step of adjusting comprises increasing the therapeutic effective dose for intrathecal administration if the GAG level in the CSF fails to decrease relative to the control after 4 doses.

In various embodiments, intrathecal administration according to the invention results in no serious adverse effects in the subject. In various embodiments, intrathecal administration according to the invention does not require an immunosuppressant.

In particular embodiments, the present invention provides a method of treating Hunter syndrome comprising administering intrathecally to a subject in need of treatment a recombinant iduronate-2-sulfatase (I2S) enzyme at a first therapeutically effective dose and administering intravenously to the subject the recombinant I2S enzyme at a second therapeutically effective dose for a treatment period sufficient to decrease glycosaminoglycan (GAG) level in the cerebrospinal fluid (CSF) relative to a control. In some embodiments, the intrathecal administration is monthly. In some embodiments, the intravenous administration is weekly.

In some embodiments, the present invention provides a recombinant iduronate-2-sulfatase (I2S) enzyme for use in a method of treating Hunter Syndrome wherein the method comprises a step of administering intrathecally to a subject in need of treatment the recombinant US enzyme at a therapeutically effective dose and an administration interval for a treatment period sufficient to improve, stabilize or reduce declining of one or more cognitive, adaptive, motor, and/or executive functions relative to a control.

In some embodiments, the present invention provides use of a recombinant iduronate-2-sulfatase (I2S) enzyme in the manufacture of a medicament for treating Hunter Syndrome wherein the treatment comprises a step of administering intrathecally to a subject in need of treatment the recombinant MS enzyme at a therapeutically effective dose and an administration interval for a treatment period sufficient to improve, stabilize or reduce declining of one or more cognitive, adaptive, motor, and/or executive functions relative to a control.

Various treatment embodiments described herein are suitable for the use of a recombinant I2S enzyme.

In some embodiments, the treatment suitable for the use of a recombinant I2S enzyme comprises administering intrathecally to a subject in need of treatment the recombinant I2S enzyme at a first therapeutically effective dose; and administering intravenously to the subject the recombinant I2S enzyme at a second therapeutically effective dose for a treatment period sufficient to improve, stabilize or reduce declining of one or more cognitive, adaptive, motor, and/or executive functions relative to a control.

In some embodiments, the present invention provides a recombinant iduronate-2-sulfatase (I2S) enzyme for use in a method of treating Hunter syndrome comprising administering intrathecally to a subject in need of treatment the recombinant I2S enzyme at a first therapeutically effective dose; and administering intravenously to the subject the recombinant I2S enzyme at a second therapeutically effective dose for a treatment period sufficient to improve, stabilize or reduce declining of one or more cognitive, adaptive, motor, and/or executive functions relative to a control.

In some embodiments, the present invention relates to use of a recombinant iduronate-2-sulfatase (I2S) enzyme in the manufacture of a medicament for treating Hunter syndrome wherein the treatment comprises administering intrathecally to a subject in need of treatment the recombinant I2S enzyme at a first therapeutically effective dose; and administering intravenously to the subject the recombinant I2S enzyme at a second therapeutically effective dose for a treatment period sufficient to improve, stabilize or reduce declining of one or more cognitive, adaptive, motor, and/or executive functions relative to a control.

In some embodiments, the present invention provides a recombinant iduronate-2-sulfatase (I2S) enzyme for use in a method of treating Hunter Syndrome wherein the method comprises a step of administering intrathecally to a subject in need of treatment the recombinant US enzyme at a therapeutically effective dose and an administration interval for a treatment period sufficient to decrease glycosaminoglycan (GAG) level in the cerebrospinal fluid (CSF) relative to a control.

In some embodiments, the present invention relates to use of a recombinant iduronate-2-sulfatase (I2S) enzyme in the manufacture of a medicament for treating Hunter Syndrome wherein the treatment comprises a step of administering intrathecally to a subject in need of treatment the recombinant I2S enzyme at a therapeutically effective dose and an administration interval for a treatment period sufficient to decrease glycosaminoglycan (GAG) level in the cerebrospinal fluid (CSF) relative to a control. Various treatment embodiments described herein are suitable for the use of a recombinant I2S enzyme.

In some embodiments, the treatment suitable for the use of a recombinant I2S enzyme comprises administering intrathecally to a subject in need of treatment the recombinant I2S enzyme at a first therapeutically effective dose; and administering intravenously to the subject the recombinant I2S enzyme at a second therapeutically effective dose for a treatment period sufficient to decrease glycosaminoglycan (GAG) level in the cerebrospinal fluid (CSF) relative to a control.

In some embodiments, the present invention provides a recombinant iduronate-2-sulfatase (US) enzyme for use in a method of treating Hunter syndrome comprising administering intrathecally to a subject in need of treatment the recombinant I2S enzyme at a first therapeutically effective dose; and administering intravenously to the subject the recombinant I2S enzyme at a second therapeutically effective dose, for a treatment period sufficient to decrease glycosaminoglycan (GAG) level in the cerebrospinal fluid (CSF) relative to a control.

In some embodiments, the present invention relates to use of a recombinant iduronate-2-sulfatase (I2S) enzyme in the manufacture of a medicament for treating Hunter syndrome, the treatment comprising administering intrathecally to a subject in need of treatment the recombinant I2S enzyme at a first therapeutically effective dose; and administering intravenously to the subject the recombinant I2S enzyme at a second therapeutically effective dose, for a treatment period sufficient to decrease glycosaminoglycan (GAG) level in the cerebrospinal fluid (CSF) relative to a control.

In some embodiments, the method, enzyme for use, or use described herein is for treating a subject has cognitive impairment. In some embodiments, a subject being treated has a GCA score or BSID-III developmental quotient less than 100, 90, 80, 70, 60, 50, 40, 30, 20, 15, 10 or not testable before the treatment. In some embodiments, a subject being treated has a GCA score or BSID-III developmental quotient declined from normal baseline less than about 40%, 35%, 30%, 25%, 20%, 15%, or 10% before the treatment. In some embodiments, a subject being treated has a GCA score or BSID-III developmental quotient ranging between about 60-100 (e.g., about 60-95, 60-90, 60-85, 60-80, 60-75, 60-70, 70-100, 70-95, 70-90, 70-85, 70-80, 80-100, 80-95, 80-90) before the treatment.

In some embodiments, the method, enzyme for use, or use described herein is for stabilizing or improving cognitive performance in a subject having Hunter Syndrome.

In some embodiments, the present invention provides a recombinant iduronate-2-sulfatase (I2S) enzyme for use in a method of stabilizing or improving cognitive performance in a subject having Hunter Syndrome wherein the method comprises a step of administering intrathecally to a subject in need of treatment the recombinant US enzyme at a therapeutically effective dose and an administration interval for a treatment period sufficient to improve, stabilize or reduce declining of one or more cognitive, adaptive, motor, and/or executive functions relative to a control.

In some embodiments, the present invention provides a recombinant iduronate-2-sulfatase (I2S) enzyme for use in a method of stabilizing or improving cognitive performance in a subject having Hunter Syndrome wherein the method comprises a step of administering intrathecally to a subject in need of treatment the recombinant US enzyme at a therapeutically effective dose and an administration interval for a treatment period sufficient to decrease glycosaminoglycan (GAG) level in the cerebrospinal fluid (CSF) relative to a control.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 5 illustrates exemplary allometrically scaled population pharmacokinetic parameters for IT-I2S delivery in pediatric subjects, after correcting for differences between non-human primates and children using a brain and body weight.

DEFINITIONS

Figure 1:
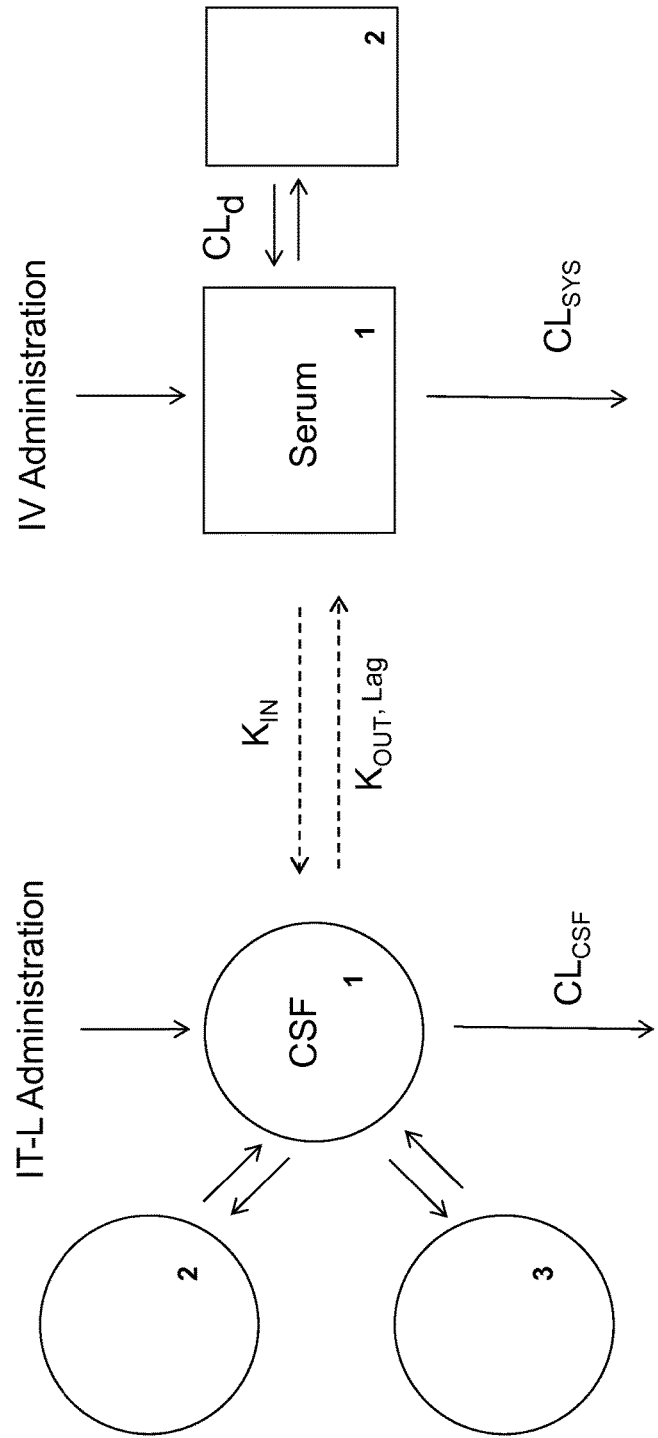
FIGS. 1-4 illustrates exemplary modeling of I2S in serum and CSF.

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, pre-conditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into the bloodstream. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between L4-L5, L3-L4, L2-L3, and/or L2-S1 regions of the spine.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue an/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity.

Therapeutically effective amount: As used herein, the term "therapeutically effective amount" refers to an amount of a therapeutic protein (e.g., replacement enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

The present invention provides, among other things, an effective method for treating Hunter syndrome, in particular, Hunter syndrome with cognitive impairment based on intrathecal administration of recombinant iduronate-2-sulfatase (I2S) enzyme. In some embodiments, the present invention provides a method of treating Hunter syndrome by administering intrathecally to a subject in need of treatment a recombinant iduronate-2-sulfatase (I2S) enzyme at a therapeutically effective dose and an administration interval for a treatment period sufficient to improve, stabilize or reduce declining of one or more cognitive, adaptive, motor, and/or executive functions relative to a control (e.g., baseline pre-treatment assessment or measurement) and/or to decrease glycosaminoglycan (GAG) level in the cerebrospinal fluid (CSF) relative to a control (e.g., baseline pretreatment assessment or measurement). In some embodiments, the intrathecal administration is performed in conjunction with intravenous administration.

Various aspects of the invention are described in detail in the following sections. The use of sections is not meant to limit the invention. Each section can apply to any aspect of the invention. In this application, the use of "or" means "and/or" unless stated otherwise.

Recombinant Iduronate-2-sulfatase (I2S) Enzyme

As used herein, the term "recombinant iduronate-2-sulfatase (I2S) enzyme" encompasses any molecule or a portion of a molecule that can substitute for naturally-occurring Iduronate-2-sulfatase (I2S) enzyme activity or rescue one or more phenotypes or symptoms associated with I2S-deficiency. In some embodiments, a recombinant I2S enzyme suitable for the invention is a polypeptide having an N-terminus and a C-terminus and an amino acid sequence substantially similar or identical to mature human I2S protein. The terms "protein" and "enzyme" are used inter-changeably in connection with I2S. A recombinant enzyme or protein is also referred to as replacement enzyme or protein in this application.

Typically, the human I2S protein is produced as a precursor form. The precursor form of human I2S contains a signal peptide (amino acid residues 1-25 of the full length precursor), a pro-peptide (amino acid residues 26-33 of the full length precursor), and a chain (residues 34-550 of the full length precursor) that may be further processed into the 42 kDa chain (residues 34-455 of the full length precursor) and the 14 kDa chain (residues 446-550 of the full length precursor). Typically, the precursor form is also referred to as full-length precursor or full-length I2S protein, which contains 550 amino acids. The amino acid sequences of the mature form (SEQ ID NO:1) having the signal peptide removed and full-length precursor (SEQ ID NO:2) of a typical wild-type or naturally-occurring human I2S protein are shown in Table 1.

Thus, in some embodiments, a recombinant I2S enzyme suitable for the present invention is mature human I2S protein (SEQ ID NO:1). In some embodiments, a suitable recombinant I2S enzyme may be a homologue or an analogue of mature human I2S protein. For example, a homologue or an analogue of mature human I2S protein may be a modified mature human I2S protein containing one or more amino acid substitutions, deletions, and/or insertions as compared to a wild-type or naturally-occurring I2S protein (e.g., SEQ ID NO:1), while retaining substantial I2S protein activity. Thus, in some embodiments, a recombinant I2S enzyme suitable for the present invention is substantially homologous to mature human US protein (SEQ ID NO:1). In some embodiments, a recombinant I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a recombinant US enzyme suitable for the present invention is substantially identical to mature human I2S protein (SEQ ID NO:1). In some embodiments, a recombinant I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a recombinant I2S enzyme suitable for the present invention contains a fragment or a portion of mature human I2S protein.

Alternatively, a recombinant US enzyme suitable for the present invention is full-length I2S protein. In some embodiments, a suitable recombinant I2S enzyme may be a homologue or an analogue of full-length human I2S protein. For example, a homologue or an analogue of full-length human I2S protein may be a modified full-length human I2S protein containing one or more amino acid substitutions, deletions, and/or insertions as compared to a wild-type or naturally-occurring full-length I2S protein (e.g., SEQ ID NO:2), while retaining substantial I2S protein activity. Thus, In some embodiments, a recombinant I2S enzyme suitable for the

TABLE 1

Human Iduronate-2-sulfatase

| | |
|---|---|
| Mature Form | SETQANSTTDALNVLLIIVDDLRPSLGCYGDKLVRSPNIDQLASHSLLFQNAFA<br>QQAVCAPSRVSFLTGRRPDTTRLYDFNSYWRVHAGNFSTIPQYFKENGYVTMSV<br>GKVFHPGISSNHTDDSPYSWSFPPYHPSSEKYENTKTCRGPDGELHANLLCPVD<br>VLDVPEGTLPDKQSTEQAIQLLEKMKTSASPFFLAVGYHKPHIPFRYPKEFQKL<br>YPLENITLAPDPEVPDGLPPVAYNPWMDIRQREDVQALNISVPYGPIPVDFQRK<br>IRQSYFASVSYLDTQVGRLLSALDDLQLANSTIIAFTSDHGWALGEHGEWAKYS<br>NFDVATHVPLIFYVPGRTASLPEAGEKLFPYLDPFDSASQLMEPGRQSMDLVEL<br>VSLFPTLAGLAGLQVPPRCPVPSFHVELCREGKNLLKHFRFRDLEEDPYLPGNP<br>RELIAYSQYPRPSDIPQWNSDKPSLKDIKIMGYSIRTIDYRYTVWVGFNPDEFL<br>ANFSDIHAGELYFVDSDPLQDHNMYNDSQGGDLFQLLMP<br>(SEQ ID NO: 1) |
| Full-Length<br>Precursor | MPPPRTGRGLLWLGLVLSSVCVALGSETQANSTTDALNVLLIIVDDLRPSLGCY<br>GDKLVRSPNIDQLASHSLLFQNAFAQQAVCAPSRVSFLTGRAPDTTRLYDFNSY<br>WRVHAGNFSTIPQYFKENGYVTMSVGKVFHPGISSNHTDDSPYSWSFPPYHPSS<br>EKYENTKTCRGPDGELHANLLCPVDVLDVPEGTLPDKQSTEQAIQLLEKMKTSA<br>SPFFLAVGYHKPHIPFRYPKEFQKLYPLENITLAPDPEVPDGLPPVAYNPWMDI<br>RQREDVQALNISVPYGPIPVDFQRKIRQSYFASVSYLDTQVGRLLSALDDLQLA<br>NSTIIAFTSDHGWALGEHGEWAKYSNFDVATHVPLIFYVPGRTASLPEAGEKLF<br>PYLDPFDSASQLMEPGRQSMDLVELVSLFPTLAGLAGLQVPPRCPVPSFHVELC<br>REGKNLLKHFRFRDLEEDPYLPGNPRELIAYSQYPRPSDIPQWNSDKPSLKDIK<br>IMGYSIRTIDYRYTVWVGFNPDEFLANFSDIHAGELYFVDSDPLQDHNMYNDSQ<br>GGDLFQLLMP<br>(SEQ ID NO: 2) | present invention is substantially homologous to full-length human I2S protein (SEQ ID NO:2). In some embodiments, a recombinant I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a recombinant I2S enzyme suitable for the present invention is substantially identical to SEQ ID NO:2. In some embodiments, a recombinant I2S enzyme suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a recombinant I2S enzyme suitable for the present invention contains a fragment or a portion of full-length human I2S protein. As used herein, a full-length I2S protein typically contains signal peptide sequence.

A recombinant I2S enzyme suitable for the present invention may be produced by any available means. For example, replacement enzymes may be recombinantly produced by utilizing a host cell system engineered to express a replacement enzyme-encoding nucleic acid. Alternatively or additionally, recombinant I2S enzymes may be produced by activating endogenous genes. Alternatively or additionally, recombinant I2S enzymes may be partially or fully prepared by chemical synthesis. Alternatively or additionally, recombinant I2S enzymes may also be purified from natural sources.

Where enzymes are recombinantly produced, any expression system can be used. To give but a few examples, known expression systems include, for example, egg, baculovirus, plant, yeast, or mammalian cells.

In some embodiments, enzymes suitable for the present invention are produced in mammalian cells. Non-limiting examples of mammalian cells that may be used in accordance with the present invention include BALB/c mouse myeloma line (NSW, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In some embodiments, recombinant I2S enzymes suitable for the present invention are produced from human cells. In some embodiments, recombinant I2S enzymes suitable for the present invention are produced from CHO cells.

In some embodiments, recombinant I2S enzymes suitable for the present invention contain a moiety that binds to a receptor on the surface of brain cells to facilitate cellular uptake and/or lysosomal targeting. For example, such a receptor may be the cation-independent mannose-6-phosphate receptor (CI-MPR) which binds the mannose-6-phosphate (M6P) residues. In addition, the CI-MPR also binds other proteins including IGF-II. In some embodiments, a recombinant I2S enzyme suitable for the present invention contains M6P residues on the surface of the protein. In some embodiments, a recombinant I2S enzyme suitable for the present invention may contain bis-phosphorylated oligosaccharides which have higher binding affinity to the CI-MPR. In some embodiments, a suitable recombinant I2S enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable recombinant I2S enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. No. 6,537,785, and U.S. Pat. No. 6,534,300, each incorporated herein by reference.

In some embodiments, recombinant I2S enzymes for use in the present invention may be conjugated or fused to a lysosomal targeting moiety that is capable of binding to a receptor on the surface of brain cells. A suitable lysosomal targeting moiety can be IGF-I, IGF-II, RAP, p97, and variants, homologues or fragments thereof (e.g., including those peptide having a sequence at least 70%, 75%, 80%, 85%, 90%, or 95% identical to a wild-type mature human IGF-I, IGF-II, RAP, p97 peptide sequence).

In some embodiments, recombinant I2S enzymes suitable for the present invention have not been modified to enhance delivery or transport of such agents across the BBB and into the CNS.

Intrathecal Administration

In some embodiments, a recombinant I2S enzyme is delivered to the CNS by administering into the cerebrospinal fluid (CSF) of a subject in need of treatment. In some embodiments, intrathecal administration is used to deliver a desired replacement enzyme into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in International Application WO2011/163648, entitled "CNS Delivery of Therapeutic Agents", the contents of which are incorporated herein by reference.

According to the present invention, a recombinant I2S enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal. In some embodiments, intrathecal administration is performed in the L5-L6, L4-L5, L3-L4, L2-L3, and/or L2-S1 regions of the spine.

Formulations for IT Delivery

In some embodiments, a desired amount of recombinant I2S enzyme is delivered in a formulation suitable for intrathecal delivery. Particularly useful formulations are capable of solubilizing high concentrations of recombinant I2S enzyme and are further characterized by improved stability and improved tolerability when administered intrathecally to the CNS of a subject in need thereof. As used herein, the term "soluble" as it relates to a recombinant I2S enzyme refers to the ability of the recombinant I2S enzyme to form a homogenous solution.

Thus, suitable formulations for intrathecal administration may contain a recombinant I2S enzyme at various concentrations. In some embodiments, suitable formulations may contain a recombinant I2S enzyme at a concentration up to about 300 mg/ml (e.g., up to about 250 mg/ml, up to about 200 mg/ml, up to about 150 mg/ml, up to about 100 mg/ml, up to about 90 mg/ml, up to about 80 mg/ml, up to about 70 mg/ml, up to about 60 mg/ml, up to about 50 mg/ml, up to about 40 mg/ml, up to about 30 mg/ml, up to about 25 mg/rill, up to about 20 mg/ml, up to about 10 mg/ml). In some embodiments, suitable formulations may contain a recombinant I2S enzyme at a concentration ranging between about 0-300 mg/ml (e.g., about 1-250 mg/ml, about 1-200 mg/ml, about 1-150 mg/ml, about 1-100 mg/ml, about 10-100 mg/nil, about 10-80 mg/ml, about 10-70 mg/ml, about 1-60 mg/ml, about 1-50 mg/ml, about 10-150 mg/ml, about 1-30 mg/ml). In some embodiments, formulations suitable for intrathecal delivery may contain a recombinant I2S enzyme at a concentration of approximately 1 mg/ml, 3 mg/ml, 5 mg/ml, 10 mg/ml, 15 mg/ml, 20 mg/ml, 25 mg/ml, 50 mg/ml, 75 mg/nil, 100 mg/ml, 150 mg/ml, 200 mg/ml, 250 mg/ml or 300 mg/ml.

In some embodiments, isotonic solutions are used. In some embodiments, slightly hypertonic solutions (e.g., up to 300 mM (e.g., up to 250 mM, 200 mM, 175 mM, 150 mM, 125 mM) sodium chloride in 5 mM sodium phosphate at pH 7.0) and sugar-containing solutions (e.g., up to 3% (e.g., up to 2.4%, 2.0%, 1.5%, 1.0%) sucrose in 5 mM sodium phosphate at pH 7.0) have been demonstrated to be well tolerated in monkeys. In some embodiments, a suitable CNS bolus formulation composition is saline (e.g., 150 mM NaCl in water).

As non-limiting examples, Table 2 below list exemplary pH and excipients suitable for maintaining the solubility and stability of a recombinant I2S in a formulation for intrathecal administration.

TABLE 2

Exemplary pH and excipients

| Parameter | Typical Range/Type | Rationale |
|---|---|---|
| pH | 4 to 8.0 | For stability<br>Sometimes also for solubility |
| Buffer type | acetate, succinate, citrate, histidine, phosphate or Tris | To maintain optimal pH<br>May also affect stability |
| Buffer concentration | 5-50 mM | To maintain pH<br>May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

In some embodiments, formulations suitable for the present invention contain an amount of buffer sufficient to maintain the optimal pH of said formulation between about 4.0-8.0, between about 5.0-7.5, between about 5.5-7.0, between about 6.0-7.0 and between about 6.0-7.5. Suitable buffers include, for example acetate, succinate, citrate, phosphate, other organic acids and tris(hydroxymethyl)aminomethane ("Tris"). Suitable buffer concentrations can be from about 1 mM to about 100 mM, from about 1 mM to about 50 mM, or from about 3 mM to about 20 mM, depending, for example, on the buffer and the desired isotonicity of the formulation. In some embodiments, a suitable buffering agent is present at a concentration of approximately 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM. In particular embodiments, a formulation suitable for the present invention contains less than about 50 mM (e.g., less than about 45 mM, 40 mM, 35 mM, 30 mM, 25 mM, 20 mM, 15 mM, 10 mM, or 5 mM) of phosphate (e.g., sodium phosphate).

In some embodiments, formulations contain an isotonicity agent to keep the formulations isotonic. As used in connection with IT delivery, by "isotonic" is meant that the formulation of interest has essentially the same osmolarity as human CSF. Isotonic formulations will generally have an osmolarity from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight.

In some embodiments, formulations may contain a stabilizing agent to protect the protein. Typically, a suitable stabilizing agent is a non-reducing sugar such as sucrose, raffinose, trehalose, or amino acids such as glycine, arginine and methionine. The amount of stabilizing agent in a formulation is generally such that the formulation will be isotonic. However, hypertonic formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10;1, or 20:1. In some embodiments, suitable for lyophilization, the stabilizing agent is also a lyoprotectant.

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristarnidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.001-0.04%, about 0.001-0.03%, about 0.001-0.02%, about 0.001-0.01%, about 0.001-0.008%, about 0.001-0.006%, about 0.001-0.004%, about 0.005-0.05%, or 0.005-0.01%). In particular, a surfactant may be present in a formulation at a concentration of approximately 0.001%, 0.002%, 0.003%, 0.004%, 0.005%, 0.006%, 0.007%, 0.008%, 0.009%, 0.01%, 0.02%, 0.03%, 0.04%, 0.05%, 0.1%, 0.2%, 0.3%, 0.4%, or 0.5%, etc.

In some embodiments, suitable formulations may further include one or more bulking agents, in particular, for lyophilized formylations. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Formulations suitable for the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

In some embodiments, formulations suitable for the present invention are in a liquid or aqueous form. In some embodiments, formulations for the present invention are lyophilized. Such lyophilized formulations may be reconstituted by adding one or more diluents thereto prior to administration to a subject. Suitable diluents include, but are not limited to, sterile water, bacteriostatic water for injection and sterile saline solution. Preferably, upon reconstitution, the therapeutic agent contained therein is stable, soluble and demonstrates tolerability upon administration to a subject Suitable formulations are characterized by their tolerability. As used herein, the terms "tolerable" and "tolerability" refer to the ability of a formulation to not elicit an adverse reaction, in particular, not to elicit a serious adverse reaction in the subject to whom such formulation is administered. In some embodiments, a formulation particularly useful for the present invention is well tolerated by the subject to whom such formulation is administered.

Additional exemplary formulations suitable for intrathecal delivery of a recombinant I2S enzyme are described in International Application WO WO2011/163649, entitled "METHODS AND COMPOSITIONS FOR CNS DELIVERY OF IDURONATE-2-SULFATASE," the contents of which are hereby incorporated by reference.

Dosing Regimen

Typically, a therapeutically effective amount of a recombinant I2S is administered in a dosing regimen that may comprise multiple unit doses. A dosing regimen suitable for any particular patient may depend upon a variety of factors including the disorder being treated and the severity of the disorder; the age, body weight, general health, sex and diet of the patient; the time of administration, and/or rate of excretion or metabolism; the duration of the treatment; and like factors as is well known in the medical arts.

Unit dose used in a dosing regimen is also referred to as a therapeutically effective dose. A therapeutically effective dose may be defined in various ways. For example, a therapeutically effective dose may be defined by the total amount of recombinant I2S enzyme administered at each time. Thus, in some embodiments, a therapeutically effective dose according to the invention is or greater than about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg per dose. In particular embodiments, a therapeutically effective dose is or greater than about 10 mg per dose. In particular embodiments, a therapeutically effective dose is or greater than about 30 mg per dose. In some embodiments, a therapeutically effective dose is less than about 50 mg, 45 mg, 40 mg, 35 mg, 30 mg, 25 mg, 20 mg, 15 mg, or 10 mg per dose. In particular embodiments, a therapeutically effective dose is less than about 30 mg per dose. In some embodiments, a therapeutically effective dose ranges between about 1-100 mg, about 5-100 mg, about 5-90 mg, about 5-80 mg, about 5-70 mg, about 5-60 mg, about 5-60 mg, about 10-100 mg, about 10-90 mg, about 10-80 mg, about 10-70 mg, about 10-60 mg, or about 10-50 mg.

Alternatively, a therapeutically effective dose may be defined by the amount of recombinant I2S enzyme administered relative to the brain weight. In some embodiments, a therapeutically effective dose according to the present invention ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is or greater than about 0.1 mg/kg brain weight, about 0.5 mg/kg brain weight, about 1.0 mg/kg brain weight, about 3 mg/kg brain weight, about 5 mg/kg brain weight, about 10 mg/kg brain weight, about 15 mg/kg brain weight, about 20 mg/kg brain weight, about 30 mg/kg brain weight, about 40 mg/kg brain weight, about 50 mg/kg brain weight, about 60 mg/kg brain weight, about 70 mg/kg brain weight, about 80 mg/kg brain weight, about 90 mg/kg brain weight, about 100 mg/kg brain weight, about 150 mg/kg brain weight, about 200 mg/kg brain weight, about 250 mg/kg brain weight, about 300 mg/kg brain weight, about 350 mg/kg brain weight, about 400 mg/kg brain weight, about 450 mg/kg brain weight, or about 500 mg/kg brain weight.

In some embodiments, the therapeutically effective dose may also be adjusted by age or body weight, especially in children under the age of 3. As one skilled in the art would appreciate, brain weights change rapidly during the first 3 years of life, reaching a plateau thereafter and body weights can be correlated in young children. See, Dekaban A S. "Changes in brain weights during the span of human life: relation of brain weights to body heights and body weights," Ann Neurol 1978; 4:345-56. Therefore, children younger than 3 years may require an adjusted (typically smaller) dose compared to older children and adults. In some embodiments, dosages used in young children may be adjusted according to the guide to the adjustment of dose based on brain weight in young children provided below (see Table 3).

TABLE 3

Change in Brain Wight During Early Human Development

| Age Group | Age (yr) | No. of Brains | Brain Weight (kg) | | | | Body Height (m) | | | | Body Weight (kg) | | | |
|---|---|---|---|---|---|---|---|---|---|---|---|---|---|---|
| | | | Mean | SD | SEM | % Change$^a$ | Mean | SD | SEM | % Change$^a$ | Mean | SD | SEM | % Change$^a$ |
| 1 | NB (0-10 d) | 241 | 0.38 | 0.09 | 0.00 | ... | 0.50 | 0.05 | 0.00 | ... | 2.95 | 0.47 | 0.03 | ... |
| 2 | 0.5 (4-8 mo) | 87 | 0.64 | 0.16 | 0.01 | 66.8 | 0.59 | 0.09 | 0.01 | 18.6 | 5.88 | 3.06 | 0.32 | 99.4 |
| 3 | 1 (9-18 mo) | 33 | 0.97 | 0.16 | 0.02 | 50.6 | 0.76 | 0.11 | 0.02 | 28.5 | 9.47 | 2.37 | 0.41 | 61.2 |
| 4 | 2 (19-30 mo) | 33 | 1.12 | 0.20 | 0.02 | 16.2 | 0.85 | 0.12 | 0.01 | 11.7 | 13.20 | 3.57 | 0.49 | 39.3 |
| 5 | 3 (31-43 mo) | 19 | 1.27 | 0.21 | 0.04 | 12.8 | 0.94 | 0.09 | 0.02 | 11.0 | 15.55 | 3.43 | 0.78 | 17.9 |
| 6 | 4-5 | 29 | 1.30 | 0.02 | 0.00 | 2.3 | 1.06 | 0.03 | 0.00 | 12.8 | 19.46 | 1.21 | 0.22 | 25.1 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

Recombinant I2S enzymes can be administered at regular intervals. In some embodiments, a therapeutically effective dose may be administered intrathecally periodically at regular intervals, e.g., once every year, once every six months (or twice a year), once every five months, once every four months, once every three months, bimonthly (once every two months), monthly (once every month or once every four weeks), once every three weeks, biweekly (once every two weeks), weekly (once every week), or at a variable interval.

Intrathecal administration may be performed in conjunction with intravenous administration of a recombinant I2S enzyme. In some embodiments, intravenous administration of a recombinant I2S enzyme is weekly. In some embodiments, the intravenous administration of a recombinant I2S enzyme is weekly except the week when the intrathecal administration is performed. In some embodiments, intravenous administration of a recombinant I2S enzyme is biweekly, once every three weeks, monthly (once every four weeks), twice a month, once every two, three, four, five, or six months. In some embodiments, intravenous administration of a recombinant I2S enzyme is at a dose of about 0.1, 0.2, 0.3, 0.4, 0.5, 0.6, 0.7, 0.8, 0.9, or 1.0 mg/kg body weight. In some embodiments, the intravenous administration of the recombinant I2S enzyme is at a dose of about 0.5 mg/kg body weight.

Device for Intrathecal Delivery

Various devices may be used for intrathecal delivery according to the present invention. In some embodiments, a device for intrathecal administration contains a fluid access port (e.g., injectable port); a hollow body (e.g., catheter)

having a first flow orifice in fluid communication with the fluid access port and a second flow orifice configured for insertion into spinal cord; and a securing mechanism for securing the insertion of the hollow body in the spinal cord. As a non-limiting example, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 nil, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

Typically, intrathecal administration can be through intermittent or continuous access to an implanted intrathecal drug delivery device (IDDD). In some embodiments, intrathecal administration is through continuous access to an implanted IDDD for, e.g., greater than 0.1, 0.2, 0.3, 0.4, 0.5, 1.0, 1.5, 2.0, 2.5, 3.0, 3.5, 4.0, 4.5, or 5.0 hours. In other embodiments, intrathecal administration is through sustained delivery, e.g., "slow release" of a recombinant I2S enzyme, to a subject for at least one, two, three, four, five, six days, or one, two, three, four weeks or longer periods of time.

As used herein, the term "sustained delivery" refers to continual delivery of a pharmaceutical formulation in vivo over a period of time following administration for, e.g., at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Immune Tolerance

Generally, intrathecal administration of a recombinant I2S enzyme according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy. Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Pharmacokinetics, Pharmacodynamics, and Bioavailability

Among other things, intrathecally delivered recombinant I2S exhibits superior pharmacokinetics, pharmacodynamics and bioavailability in a human patient. Evaluation of I2S concentration-time profiles in CSF may be evaluated directly by CSF sampling or indirectly by measuring systemic serum I2S concentration-time profiles. Typically, however, due to the limited number of clinically permissible CSF sample collections, I2S pharmacokinetic and pharmacodynamics profiles are evaluated indirectly by sampling the blood periodically. The following standard abbreviations are used to represent the associated pharmacokinetic parameters.

$AUC_{inf}$ Area under the plasma concentration versus time curve up to the last measurable concentration plus the AUC, calculated using the linear trapezoidal rule from the zero time point to the last quantifiable concentration and extrapolated from the last measurable concentration ($C_{last}$ at $t_{last}$) to infinity: $AUC_{INFobs} = AUC_{0-tlast} + C_{last}/\text{Lambda } z$ (where $\lambda z$ is the first order rate constant associated with the terminal (log-linear) portion of the curve)

$AUC_{0-12}$ Area under the curve between the time of dose and the 12 h time point $AUC_{0-24}$ Area under the curve between the time of dose and the 24 h time point $AUC_{ss}$ Exposure at steady state for the dosing interval F Fraction available (bioavailability):

$$F = [AUC_{oral}] \cdot dose_{iv} / [AUC_{iv}] \cdot dose_{oral}$$

CL Clearance

CLr Renal clearance, calculated for the 24-hour steady-state period according to $$CLr = \frac{Ue(0-24)}{AUC(0-24)}$$

Where Ue is excreted drug

Cl/F Apparent total body clearance as a function of bioavailability $$CL/F = \frac{Dose}{AUC(0-24)}$$

$V_{ss}$ Steady state volume of distribution
$V_d$ Volume of distribution
$V_z/F$ Apparent terminal phase volume of distribution as a function of bioavailability $$Vz/F = \frac{Dose}{\lambda z \times AUC(0-24)}$$

$t_{1/2}$ Terminal half-life ($HL_{\lambda z}$), calculated by the equation $t\frac{1}{2} = 0.693/k_{el}$ $C_{max}$ The maximum observed concentration, obtained directly from the plasma concentration time profile $T_{max}$ The time of $C_{max}$; at more than one time point, the first is chosen $\lambda z$ elimination rate constant, calculated as the negative of the slope of the terminal log-linear segment of the plasma concentration-time curve, where slope is determined from a linear regression of the natural logarithm of the terminal plasma concentrations against time; at least 3 terminal plasma concentration time points, beginning with the final concentration≥LOQ, will be selected for the determination of $\lambda z$ and the regression will need coefficient of determination ($r^2$)≥0.9000.

$k_{el}$ The terminal elimination rate constant will be obtained from the slope of the line, fitted by linear least squares regression, through the terminal points of the log (base e) concentration-time profiles.

Typically, actual blood sample collection times relative to the start of I2S intrathecal administration are used in the IT PK analysis. For example, blood samples are typically collected within 15 or 30 minutes prior to I2S intrathecal administration (pre-injection baseline or time 0) and at 0.5, 1, 1.5, 2, 3, 4, 6, 8, 12, 24, 30, 36, 48, 60, 72, 84, 96, 108, 120, 132, 144, 156, 168 or 180 hours following intrathecal administration. If IT is administered in conjunction with IV administration, for IV PK analysis, blood samples are collected 15 or 30 minutes prior to IV infusion (pre-infusion baseline or time 0) and at 0.5, 1, 1.5, 2, 2.5, and 3 hours during the infusion (if the infusion is 3 hours long), and at 3.5, 4, 5, 6, 7, 9, 11, and 24 hours following the initiation of IV infusion.

Various methods may be used to measure I2S protein concentration in serum. As a non-limiting example, enzyme-linked immunosorbent assay (ELISA) methods are used.

Pharmacokinetic parameters for I2S can be determined using compartmental, noncompartmental, or population-based (i.e., POP-PR) analysis methods known in the art. In some embodiments, pharmacokinetic parameters for I2S are determined by noncompartmental analysis using Phoenix Version 6.1 (Pharsight Corporation, Mountain View, Calif.).

Pharmacokinetic parameters may be evaluated at any stage during the treatment, for example, at week 1, week 2, week 3, week 4, week 5, week 6, week 7, week 8, week 9, week 10, week 11, week 12, week 13, week 14, week 15, week 16, week 17, week 18, week 19, week 20, week 21, week 22, week 23, week 24, or later. In some embodiments, pharmacokinetic parameters may be evaluated at month 1, month 2, month 3, month 4, month 5, month 6, month 7, month 8, month 9, month 10, month 11, month 12, month 13, month 14, month 15, month 16, month 17, month 18, month 19, month 20, month 21, month 22, month 23, month 24, or later during the treatment.

Typically, as described in the Examples section, following intrathecal administration, serum concentrations of I2S increased slowly.

In some embodiments, the systemic bioavailability of I2S following intrathecal administration ranges from about 20-90% (e.g., about 20-80%, 20-75%, 20-70%, 20-65%, 60-60%, 20-55%, 20-50%, 30-90%, 30-80%, 30-75%, 30-70%, 30-65%, 30-60%, 30-55%, 30-50%, 40-90%, 40-80%, 40-75%, 40-70%, 40-65%, 40-60%, 40-55%, 40-50%, 50-90%, 50-80%, 50-75%, 50-70%, 50-65%, 50-60%). In some embodiments, the systemic bioavailability of I2S following intrathecal administration is or greater than about 20%, 25%, 30%, 35%, 40%, 45%, 50%, 55%, 60%, 65%, 70%, 75%, 80%, 85%, or 90%.

In some embodiments, various dosing regimens described herein (i.e., a therapeutically effective dose, administered regularly at the administration interval) results in serum $AUC_{ss}$ of the recombinant I2S enzyme within a range from approximately 200,000 min·ng/mL to approximately 1,000,000 min·ng/mL (e.g., from approximately 250,000 min·ng/mL to approximately 900,000 min·ng/mL, from approximately 300,000 min·ng/mL to approximately 800,000 min·ng/mL, from approximately 350,000 min·ng/mL to approximately 700,000 min·ng/mL, from approximately 400,000 min·ng/mL to approximately 600,000 min·ng/mL).

In some embodiments, various dosing regimens described herein (i.e., a therapeutically effective dose, administered regularly at the administration interval) results in maximum serum concentration ($C_{max}$) of the recombinant I2S enzyme within a range from approximately 60 to approximately 300 ng/mL (e.g., from approximately 70 to approximately 250 ng/mL, from approximately 70 to approximately 200 ng/mL, from approximately 70 to approximately 150 ng/mL, from approximately 80 to approximately 250 ng/mL, from approximately 80 to approximately 200 ng/mL, from approximately 80 to approximately 150 ng/mL, from approximately 90 to approximately 250 ng/mL, from approximately 90 to approximately 200 ng/mL, from approximately 90 to approximately 150 ng/mL).

Reducing GAG Levels

As described above, Hunter syndrome, or Mucopolysaccharidosis II (MPS II), is an X-linked heritable metabolic disorder resulting from a deficiency of the enzyme iduronate-2-sulfatase (I2S). I2S is localized to lysosomes and plays an important role in the catabolism of glycosaminoglycans (GAGs) heparan- and dermatan-sulfate. In the absence of enzyme, these substrates accumulate within cells, ultimately causing engorgement, followed by cellular death and tissue destruction. Due to the widespread expression of enzyme, multiple cell types and organ systems are affected in MPS II patients.

Thus, Hunter syndrome is characterized by an accumulation of glycosaminoglycans (GAG) in the lysosomes of affected cells including both somatic and CNS cells. A patient suffering from or susceptible to Hunter syndrome has abnormally high levels of GAG in the CSF, urine and/or blood. For example, in urine, the normal reference range of uGAG levels, depending on the age, ranges between 57 and 487 ug/mg creatinine. However, Hunter syndrome patients without treatment may have high uGAG levels, e.g., higher than about 1000 μg/mg creatinine, 1050 μg/mg creatinine, 1100 μg/mg creatinine, 1150 μg/mg creatinine, 1200 μg/mg creatinine, 1250 μg/mg creatinine, 1300 μg/mg creatinine, 1350 μg/mg creatinine, 1400 μg/mg creatinine, 1450 μg/mg creatinine, or 1500 μg/mg creatinine.

Patients with Hunter syndrome and cognitive impairment, typically also have abnormally high levels of GAGs in the CSF. For example, the CSF GAG level in healthy children is typically below the lower limit of quantification (LLOQ) and in young healthy adults, the CSF GAG level is typically between lower than LLOQ to about 95 ng/ml. However, in a Hunter syndrome patient, the baseline pre-treatment measurement of the CSF GAG level may be greater than about 300, 400, 500, 600, 700, 800, 900, 1000, 1500, or 2000 ng/ml.

Thus, changes from baseline in the concentrations of GAG in the urine, blood and/or CSF may be used as a biomarker indicative of the pharmacodynamics activity and/or efficacy of I2S in vivo. In particular, changes from baseline in the concentrations of GAG in CSF may be used as a biomarker indicative of the pharmacodynamics activity of I2S in CSF after intrathecal administration or as endpoints for efficacy. For example, according to the present invention, a recombinant I2S enzyme is administered intrathecally at a therapeutically effective dose and an administration interval for a treatment period sufficient to decrease glycosaminoglycan (GAG) level in the cerebrospinal fluid (CSF) and/or urine relative to a control. As used herein, the term "decrease," or equivalent such as "reduce," or grammatical equivalents, indicate a measurement of GAG level that is relative to a baseline measurement, such as a measurement in the same individual prior to initiation of the treatment, or a measurement in a control individual (or multiple control individuals) in the absence of the treatment. A "control individual" is an individual afflicted with Hunter syndrome as the individual being treated, who is about the same age as the individual being treated (to ensure that the stages of the disease in the treated individual and the control individual(s) are comparable).

In some embodiments, intrathecal administration of a recombinant I2S enzyme according to the present invention results in a reduction of the GAG level in CSF, urine and/or blood by about 5%, 10%, 15%, 20%, 25%, 30%, 35%, 40%, 45%, 50%, 55%, 60%, 65%, 70%, 75%, 80%, 85%, 90%, 95%, 100% or more as compared to a control (e.g., baseline measurement). In some embodiments, intrathecal administration of a recombinant I2S enzyme according to the present invention results in a reduction of the GAG level in CSF, urine and/or blood by at least 1-fold, 2-fold, 3-fold, 4-fold, 5-fold, 6-fold, 7-fold, 8-fold, 9-fold or 10-fold as compared to a control (e.g., baseline measurement).

In some embodiments, intrathecal administration of a recombinant I2S enzyme according to the present invention results in the GAG level in the CSF lower than about 1000 ng/ml (e.g., lower than about 900 ng/ml, 800 ng/ml, 700 ng/ml, 600 ng/ml, 500 ng/ml, 400 ng/ml, 300 ng/ml, 200 ng/ml, 100 ng/ml, 50 ng/ml, 10 ng/ml, or 1 ng/ml).

In some embodiments, intrathecal administration of a recombinant US enzyme according to the present invention results in the GAG level in urine lower than about 1000 μg/mg creatinine (e.g., lower than about 900 μg/mg creatinine, 800 μg/mg creatinine, 700 μg/mg creatinine, 600 μg/mg creatinine, or 500 μg/mg creatinine).

Various methods for measuring the GAG level in CSF or urine are known in the art and can be used to practice the present invention. Exemplary methods include, but are not limited to, electro-spray ionization-tandem mass spectrometry (with and without liquid chromatography), HPLC or LC-MS based assays as described in Lawrence R. et al. Nat. Chem. Biol.; 8(2):197-204. In some embodiments, the GAG level is measured at the end of each dosing cycle (e.g., at the end of each month following the monthly intrathecal administration), i.e., immediately before the next dosing. The GAG level may also be measured at the beginning or in the middle of each dosing cycle (e.g., at the beginning or middle of each month following the monthly intrathecal administration).

In some embodiments, a reduction of the GAG level in CSF described herein is achieved after a treatment period of at least 1, 2, 3, 4, 5, 6, 8, 10, 12, 18, 24, or more months. In some embodiments, a reduction of the GAG level in CSF described herein is achieved after a treatment period of at least 1, 2, 3, 4, 5, 6, 7, 8, 9, 10 years or longer.

In various embodiments, intrathecal administration of a recombinant I2S enzyme may be used to maintain the GAG level in CSF at a low level (e.g., lower than about 1000 ng/ml, 900 ng/ml, 800 ng/ml, 700 ng/ml, 600 ng/ml, 500 ng/ml, 400 ng/ml, 300 ng/ml, 200 ng/ml, 100 ng/ml, 50 ng/ml, 10 ng/ml, or 1 ng/ml) for more than 3, 4, 5, 6, 8, 10, 12 months, or 1, 2, 3, 4, 5, 6, 7, 8, 9, 10, years, or the life-time of the patient being treated. In various embodiments, intrathecal administration of a recombinant I2S enzyme may be used to maintain the GAG level in urine at a low level (e.g., lower than about 1000 µg/mg creatinine, 900 µg/mg creatinine, 800 µg/mg creatinine, 700 µg/mg creatinine, 600 µg/mg creatinine, or 500 µg/mg creatinine) for more than 3, 4, 5, 6, 8, 10, 12 months, or 1, 2, 3, 4, 5, 6, 7, 8, 9, 10, years, or the life-time of the patient being treated.

In various embodiments, the GAG level in CSF, urine and/or blood may also be used as a biomarker to monitor and/or optimize the treatment. For example, the dose and/or administration interval for intrathecal and/or intravenous administration (if the intrathecal administration is used in conjunction with intravenous administration) may be adjusted based on the GAG level in the CSF, urine and/or blood. In some embodiments, the dose for intrathecal administration may be increased if the GAG level in the CSF or urine or blood fails to decrease relative to the baseline control after 6, 5, 4, or 3 doses. In particular embodiments, the dose for intrathecal administration may be increased if the GAG level in the CSF, urine or blood fails to decrease relative to the baseline control after 4 doses.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with the same disease, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having the disease or having the potential to develop the disease. In some embodiments, a subject being treated is at least 6 moths old, 12 months old, 18 months old, 2 years old, 2.5 years old, 3 years old, 3.5 years old, 4 years old, 4.5 years old, or 5 years old. In some embodiments, a subject being treated is younger than 5, 4.5, 4, 3.5, 3, 2.5, 2, or 1.5 years old. In some embodiments, a subject in need of treatment has a GAG level in the CSF greater than about 300, 400, 500, 600, 700, 800, 900, 1000, 1500, or 2000 ng/ml before the treatment. In some embodiments, a subject in need of treatment has a GAG level in urine higher than about 1000 µg/mg creatinine, 1050 µg/mg creatinine, 1100 µg/mg creatinine, 1150 µg/mg creatinine, 1200 µg/mg creatinine, 1250 µg/mg creatinine, 1300 µg/mg creatinine, 1350 µg/mg creatinine, 1400 µg/mg creatinine, 1450 µg/mg creatinine, or 1500 µg/mg creatinine.

Other biomarkers of Hunter syndrome may also be used to practice the present invention, for example, heparin cofactor II-thrombin complex as described in D. R. Randall et al., "Heparin cofactor II-thrombin complex: A biomarker of MPS disease," Molecular Genetics and Metabolism 94 (2008) 456-461, the contents of which are hereby incorporated by reference.

Treatment of Cognitive Impairment

A defining clinical feature of Hunter syndrome is central nervous system (CNS) degeneration, which results in cognitive impairment (e.g., decrease in IQ). Additionally, MRI scans of affected individuals have revealed white matter lesions, dilated perivascular spaces in the brain parenchyma, ganglia, corpus callosum, and brainstem; atrophy; and ventriculomegaly (Wang et al. Molecular Genetics and Metabolism, 2009). The disease typically manifests itself in the first years of life with organomegaly and skeletal abnormalities. Some affected individuals experience a progressive loss of cognitive function, with most affected individuals dying of disease-associated complications in their first or second decade.

Among other things, the present invention may be used to effectively treat cognitive impairment in Hunter syndrome patients. In some embodiments, treatment according to the present invention results in improved cognitive performance of a patient suffering from Hunters Syndrome. As used herein, cognitive performance includes, but is not limited to, cognitive, adaptive, motor, and/or executive functions. Thus, in some embodiments, a method according to the invention may be used to improve, stabilize or reduce declining of one or more cognitive, adaptive, motor, and/or executive functions relative to a control.

Assessment of Cognitive Performance

Typically, cognitive performance may be assessed by a cognitive performance instrument. As used herein, the term "cognitive performance instrument" includes a cognitive performance test that can be used to evaluate, classify and/or quantify one or more cognitive, adaptive motor and/or executive functions in a subject. As will be understood by those skilled in the art, such a test may be questionnaire or survey filled out by a patient, caregiver, parent, teacher, therapist or psychologist. Exemplary cognitive performance instruments suitable for assessing cognitive, adaptive motor and/or executive functions are described below.

Differential Abilities Scale (DAS-II)

In some specific embodiments, the cognitive performance instrument is the Differential Ability Scale. The Differential Ability Scale, as the name implies, was developed specifically to be suitable for patients with various types of impairment. The DAS-II is a cognitive test that is designed primarily as a profile test which yields scores for a wide range of abilities, measured either by subtests or composites. However, it has been used as a general test of cognitive ability, including in severely affected populations. The DAS-II comprises 2 overlapping batteries. The Early Years battery is designed for children ages 2 years 6 months through 6 years 11 months. The School-Age Battery is designed for children ages 7 years 0 months through 17 years 11 months. A key feature of these batteries is that they were fully co-normed for ages 5 years 0 months through 8 years 11 months. In consequence, children ages 7 years 0 months through 8 years 11 months can be given the Early Years battery if that is considered more developmentally appropriate for an individual than the School-Age Battery. Similarly, more able children ages 5 years 0 months through 6 years 11 months can be given the School-Age Battery. As a result, the test accommodates all 5 to 8 year old children (i.e., 5 years 0 months through 8 years 11 months) at the extremes of the ability range.

Figure 19:
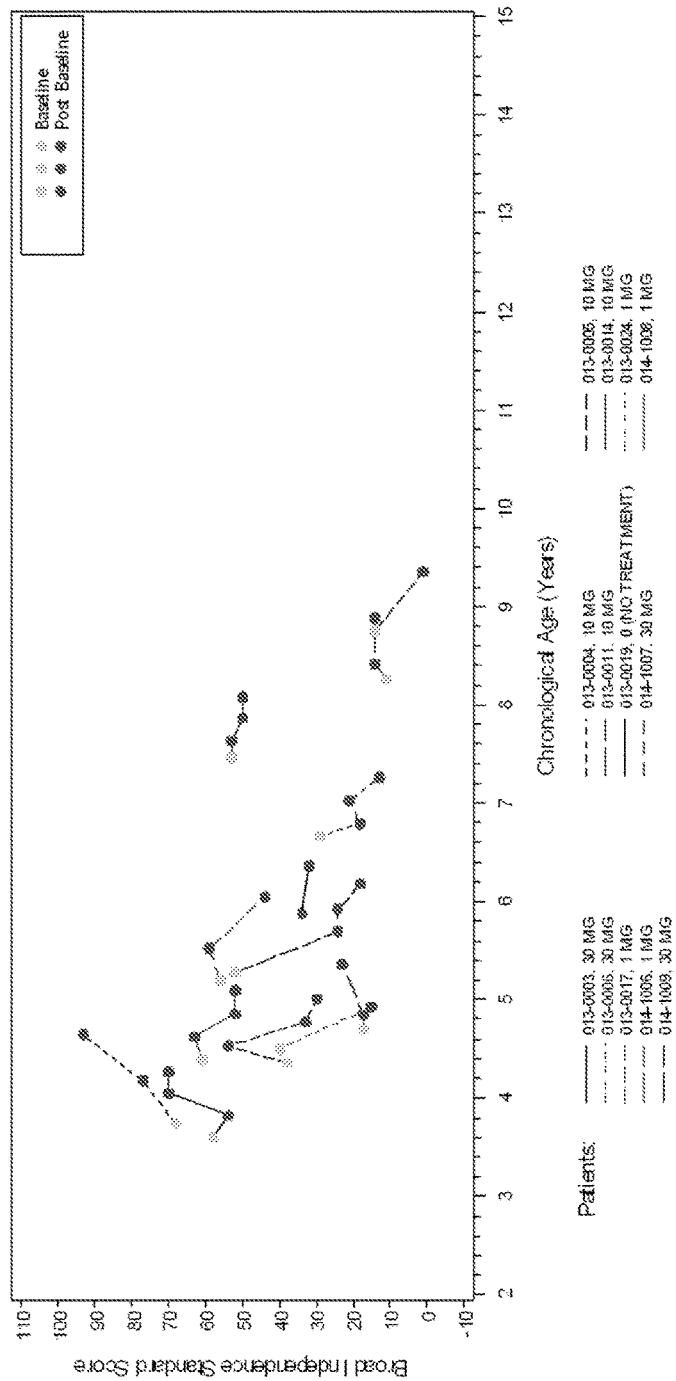
FIG. 19 illustrates exemplary individual patient SIB-R Broad standard Independence standard scoreby chronological age.

The DAS-II has been validated and normed in the US population and in the British population (as the BAS, or British Abilities Scales). A Spanish version, intended for use in Spain and Spanish-speaking Latin America, is expected to become available in the fall of 2012. The DAS-II incorporates "tailored testing" to enable examiners to select the most appropriate items for a child. This has two major advantages. First, it enables the measure to be both accurate and very time-efficient, which is a major advantage for the examiner. Second, it makes testing shorter and less tiring for the child and often enables the child to discontinue a subtest before having experienced a string of consecutive failures— an advantage for the child, as the tests are more enjoyable and motivating. Without being a limiting example, Table 4 discloses a plurality of subtest capable of measuring different cognitive abilities, for a subject undergoing enzyme replacement therapy. FIG. 19 shows the same subtests and the age ranges at which they are normed.

TABLE 4

List of Cognitive Performance Instruments

| Subtest | Abbreviation | Abilities Measured |
| --- | --- | --- |
| Copying | Copy | Visual-perceptual matching and fine-motor coordination in copying line drawings |
| Early number concepts | ENC | Knowledge of pre-numerical and numerical concepts |
| Matching letter-like forms | MLLF | Visual discrimination among similar shapes |
| Matrices | Mat | Nonverbal reasoning: perception and application of relationships among abstract figures |
| Naming vocabulary | NVoc | Expressive language; knowledge of names |
| Pattern construction | PCon | Visual-perceptual matching, especially of spatial orientation, in copying block patterns. Nonverbal reasoning and spatial visualization in reproducing designs with colored blocks |
| Pattern Construction (alt) | PCon(A) | The same abilities for Pattern construction without a time constraint |
| Phonological processing | PhP | Knowledge of sound structure of the English language and the ability to manipulate sound |
| Picture similarities | PSim | Nonverbal reasoning shown by matching pictures that have a common element or concept |
| Rapid naming | RNam | Automaticity of integration of visual symbols with phonologically referenced naming |
| Recall of designs | RDes | Short-term recall of visual and spatial relationships through reproduction of abstract figures |
| Recall of digits forward | DigF | Short-term auditory memory and oral recall of sequences of numbers |
| Recall of digits backward | DigB | Short-term auditory memory and oral recall of sequences of numbers |
| Recall of objects-Immediate | RObI | Short-term recall of verbal and pictorial information |
| Recall of objects-Delayed | RObD | Intermediate-term recall of verbal and pictorial information |
| Recall of sequential order | SeqO | Short-term recall of verbal and pictorial information |
| Recognition of pictures | RPic | Short-term, nonverbal visual memory measure through recognition of familiar objects |
| Sequential and quantitative reasoning | SQR | Detection of sequential patterns in figures or numbers |
| Speed of information processing | SIP | Quickness in performing simple mental operations |
| Verbal comprehension | VCom | Receptive language: understanding of oral instructions involving basic language concepts |
| Verbal similarities | VSim | Verbal reasoning and verbal knowledge |
| Word definitions | WDef | Knowledge of word meanings as demonstrated through spoken language |

Scales of Independent Behavior-Revised (SIB-R)

In some specific embodiments, the cognitive performance instrument is the scales of independent behavior-revised. The Scales of Independent Behavior-Revised (SIB-R) is a measure of adaptive behavior comprising 14 subscales organized into 4 adaptive behavior clusters: (1) Motor skills, (2) Social Interaction/Communication, (3) Personal Living skills and (4) Community and Living skills. For each item, the rater is presented with statements that ask them to evaluate the ability and frequency with which the individual being rated can or does perform, in its entirety, a particular task without help or supervision. The individual's performance is rated on a 4-point Likert scale, with responses including (0): Never or Rarely—even if asked; (1) Does, but not Well—or about one quarter of the time—may need to be asked; (2) does fairly well—or about three quarters of the time—may need to be asked; (3) does very well—always or almost always without being asked.

It also measures 8 areas of problem behavior. The SIB-R provides norms from infancy through to the age of 80 and above. It has been used in children with autism and intellectual disability. Some experts consider that one of the strengths of the SIB-R is that has application for basic adaptive skills and problem behaviors of children with significant cognitive or autistic spectrum disorders and can map to American Association of Mental Retardation levels of support. The SIB-R is considered to be much less vulnerable to exaggeration than some other measures of adaptive behaviors.

Bayley Scales of Infant Development

In some embodiments, the evaluation of developmental function may be performed using one or more developmental performance instruments. In some embodiments, the developmental performance instrument is the Bayley Scales of Infant Development (BSID-III). The Bayley Scales of Infant Development is a standard series of measurements used primarily to assess the motor (fine and gross), language (receptive and expressive), and cognitive development of infants and toddlers ages 0-3. This measure consists of a series of developmental play tasks and takes between 45-60 minutes to administer. Raw scores of successfully completed items are converted to scale scores and to composite scores. These scores are used to determine the child's performance compared with norms taken from typically developing children of their age (in months). The assessment is often used in conjunction with the Social-Emotional Adaptive Behavior Questionnaire. Completed by the parent or caregiver, this questionnaire establishes the range of adaptive behaviors that the child can currently achieve and enables comparison with age norms.

Wechsler Intelligence Scale for Children (WISC)

In some embodiments, the Wechsler Intelligence Scale for Children (WISC) may be performed. Typically, the WISC test is an individually administered intelligence test for children, in particular, children between the ages of 6 and 16 inclusive. In some embodiments, the WISC test can be completed without reading or writing. An WISC score generally represents a child's general cognitive ability.

Vineland Adaptive Behavior Scales

Figure 20:
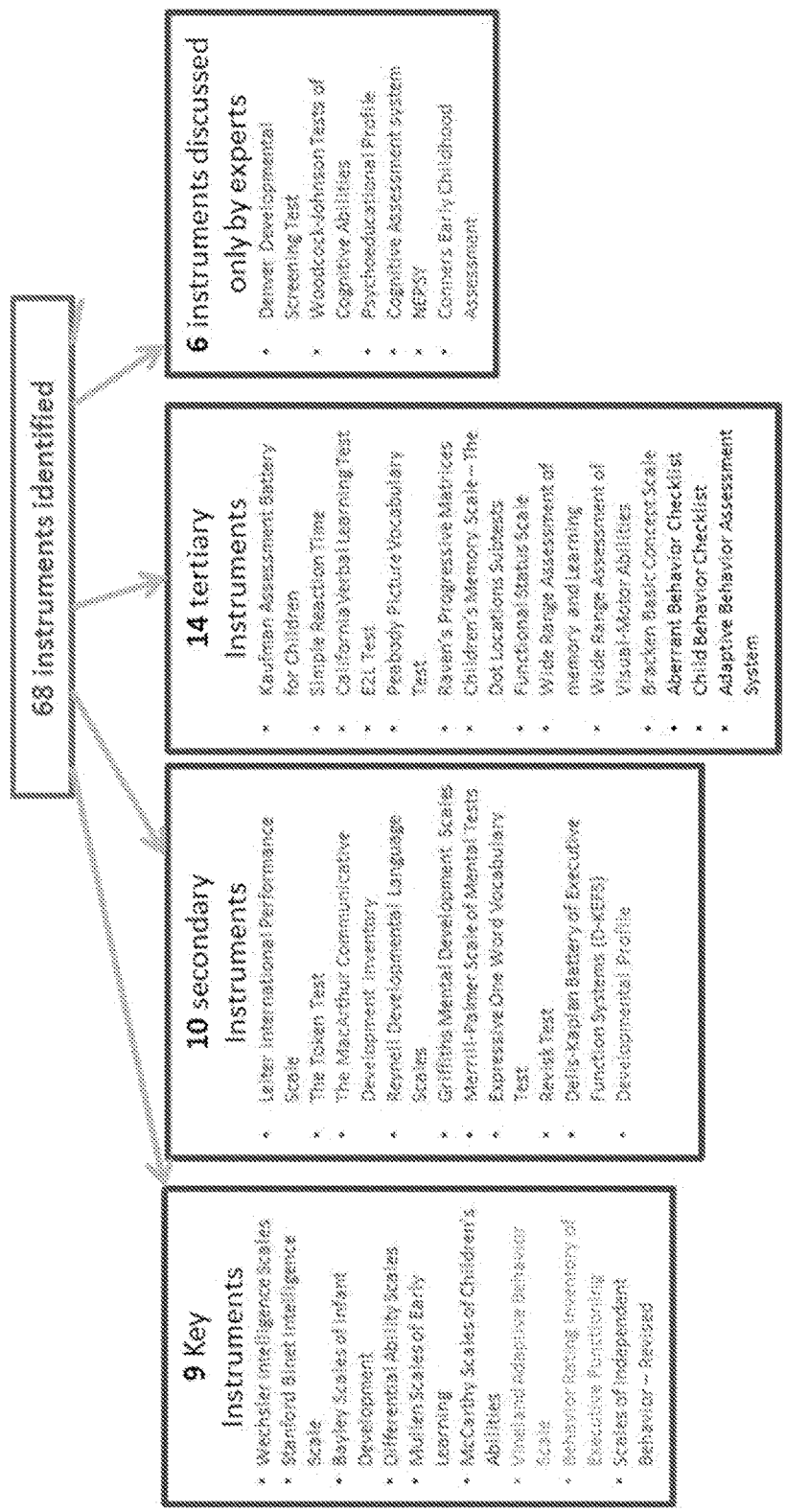
FIG. 20 illustrates additional exemplary instruments for assessing cognitive performance.
Figure 21:
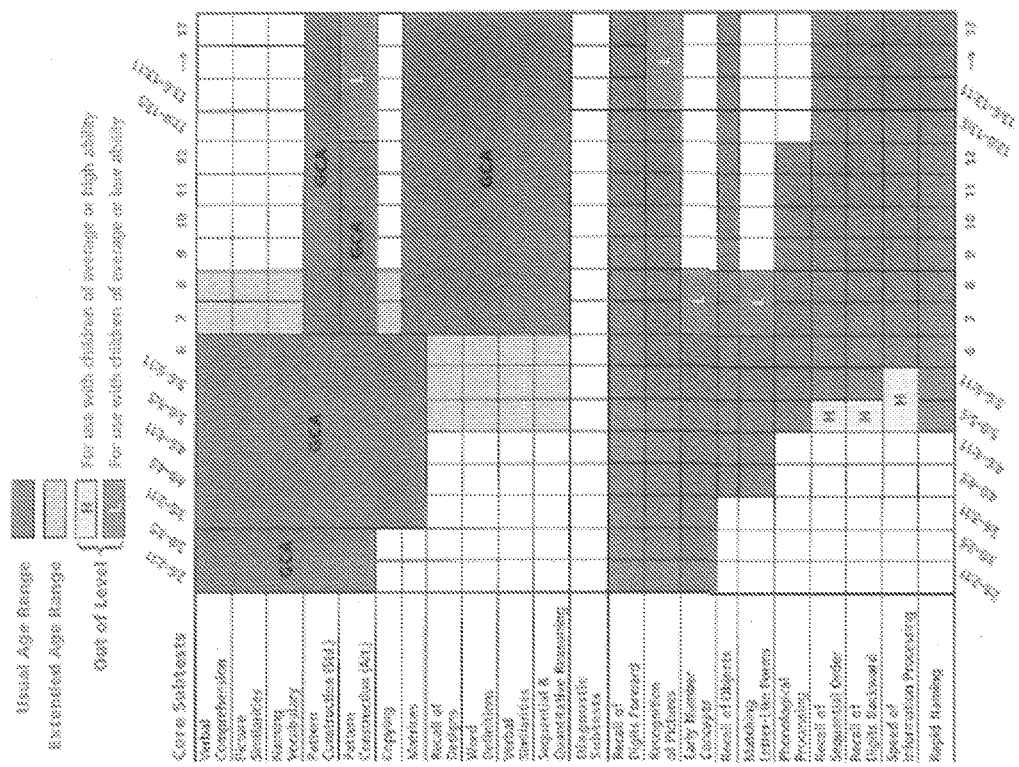
FIG. 21 illustrates the subtests of the DAS-II.

In some embodiments, Vineland Adaptive Behavior Scales are performed. Typically, Vineland Adaptive Behavior Scales measure a person's adaptive level of functioning. Typically, the content and scales of Vineland Adaptive Behavior Scales are organized within a three domain structure: Communication, Daily Living, and Socialization. This structure corresponds to the three broad Domains of adaptive functioning recognized by the American Association of Mental Retardation (AAMR, 2002): Conceptual, Practical, and Social. In addition, Vineland Adaptive Behavior Scales offer a Motor Skills Domain and an optional Maladaptive Behavior Index to provide more in-depth information Additional exemplary cognitive performance instruments suitable for the present invention are listed in FIGS. 19 and 20.

Brain Structure Volume

In addition to various standardized tests described herein, brain structure volume may be used to assess brain health and function. For example, such analysis may be performed by examining total cortical gray matter volume, derived from automated analysis of serial brain magnetic resonance imaging scans (MRIs).

Cognitive Improvement

In various embodiments, the present invention provides methods for treating Hunters syndrome, in particular, by improving cognitive performance. For example, a method according to the invention may include a step of administering intrathecally to a subject in need of treatment a recombinant iduronate-2-sulfatase (I2S) enzyme at a therapeutically effective dose and an administration interval for a period sufficient to improve, stabilize or reduce declining of one or more cognitive, adaptive, motor, and/or executive functions relative to a control. As used herein, the terms "improve," "stabilize" or "reduce," or grammatical equivalents, indicate an assessment or measurement of cognitive, adaptive, motor, and/or executive functions (e.g., cognitive test scores) that are relative to a baseline assessment or measurement, such as an assessment or measurement in the same individual prior to initiation of the treatment described herein, or an assessment or measurement in a control individual (or multiple control individuals) in the absence of the treatment described herein. A "control individual" is an individual afflicted with Hunter Syndrome as the individual being treated, who is about the same age as the individual being treated (to ensure that the stages of the disease in the treated individual and the control individual(s) are comparable).

Various cognitive instruments including those described herein may be used to assess one or more cognitive, adaptive, motor, and/or executive functions. In some embodiments, the Differential Ability Scales—Second Edition (DAS-II) is used. The DAS-II assessment may be presented as a raw score, cluster score, standardized score, percentile age equivalent, or developmental quotient. In some embodiments, the DAS-II assessment is presented as a general conceptual ability (GCA) score. In some embodiments, Bayley Scales of Infant Development Version III (BSID-III) is used.

In various embodiments, intrathecal administration of the recombinant I2S enzyme results in improved GCA score or BSID-III developmental quotient relative to a control (e.g., baseline pre-treatment score) after a treatment period of or longer than 3, 4, 5, 6, 7, 8, 9, 10, 11, 12, 18 months, or 1, 2, 3, 4, 5, 10 years. For example, intrathecal administration of the recombinant I2S enzyme may improve the GCA score or BSID-III developmental quotient by 5, 10, 11, 12, 13, 14, 15, 20, 25, 30 points or more as compared to a control (e.g., baseline pre-treatment score) after a treatment period of or longer than 3, 4, 5, 6, 7, 8, 9, 10, 11, 12, or 18 months. In some embodiments, intrathecal administration of the recombinant I2S enzyme may improve the GCA score or BSID-III developmental quotient by 10%, 15%, 20%, 25%, 30%, 35%, 40%, 45%, 50% or more as compared to a control (e.g., baseline pre-treatment score) after a treatment period of or longer than 3, 4, 5, 6, 7, 8, 9, 10, 11, 12, or 18 months. In some embodiments, intrathecal administration of the recombinant I2S enzyme may result in an improved GCA score or BSID-III developmental quotient within the range of 70-105 (e.g., 70-100, 70-95, 70-90, 75-105, 75-100, 75-95, 75-90, 80-105, 80-100, 80-95, 80-90) after a treatment period of or longer than 3, 4, 5, 6, 7, 8, 9, 10, 11, 12, or 18 months. In some embodiments, intrathecal administration of the recombinant I2S enzyme may result in an improved GCA score or BSID-III developmental quotient of or greater than 70, 75, 80, 85, 86, 87, 88, 89, 90 points, or greater after a treatment period of or longer than 3, 4, 5, 6, 7, 8, 9, 10, 11, 12, or 18 months. Typically, intrathecal administration of the recombinant I2S enzyme may also maintain the improved score for a period of or longer than 3, 6, 9, 12, 15, 18, 21, 24, 27, 30, 33, or 36 months. As used herein, maintaining the GCA score or BSID-III developmental quotient means the change of GCA score or BSID-III developmental quotient is less than 10, 9, 8, 7, 6, or 5 points within a period of 3, 6, 8, 10, 12 months or the change of the GCA score or BSID-III developmental quotient over a period of 3, 6, 8, 10, 12 months within 20%, 15%, 10%, 5% of the mean over such period.

In some embodiments, intrathecal administration of the recombinant I2S enzyme results in stabilization of the GCA score or BSID-III developmental quotient relative to the baseline pre-treatment assessment after a treatment period of or longer than 3, 4, 5, 6, 7, 8, 9, 10, 11, 12, 18 months, or 1, 2, 3, 4, 5, 10 years. As used herein, stabilization of the GCA score or BSID-III developmental quotient means the change of GCA score or BSID-III developmental quotient from the baseline is less than 10, 9, 8, 7, 6, or 5 points within 3, 6, 8, 10, 12 months or the change of the GCA score or BSID-III developmental quotient over a period of 3, 6, 8, 10, 12 months within 20%, 15%, 10%, 5% of the mean over such period. In some cases, stabilization of the GCA score or developmental quotient means the change of GCA score or BSID-III developmental quotient from the baseline is less than 20%, 15%, 10%, 5% within 3, 6, 8, 10, 12 months. In some embodiments, the stabilization happens after the initial declining of the GCA score or BSID-III developmental quotient. For example, stabilization may follow after no less than 40%, 35%, 30%, 25%, 20%, 15%, or 10% declining of the GCA score or BSID-III developmental quotient from the baseline. In some embodiments, intrathecal administration of the recombinant I2S enzyme may stabilize the GCA score or BSID-III developmental quotient for a period of or longer than 3, 6, 9, 12, 15, 18, 21, 24, 27, 30, 33, or 36 months. In some embodiments, intrathecal administration of the recombinant I2S enzyme may stabilize the GCA score or BSID-III developmental quotient for a period of 3-36 months (e.g., 3-33, 3-30, 3-27, 3-24, 3-21, 3-18, 3-15, 3-12, 3-9, 3-6, 6-36, 6-33, 6-30, 6-27, 6-24, 6-21, 6-18, 6-15, 6-12, 6-9 months).

In some embodiments, intrathecal administration of the recombinant I2S enzyme results in reduced declining of the GCAscore or BSID-HI developmental quotient relative to a control (e.g., the baseline pre-treatment score) after a treatment period of or longer than 3, 4, 5, 6, 7, 8, 9, 10, 11, 12, 18 months, or 1, 2, 3, 4, 5, 10 years. For example, the intrathecal administration of the recombinant I2S enzyme may result in the annual decline of the GCA score or BSID-III developmental quotient less than about 20, 19, 18, 17, 16, 15, 14, 13, 12, 11, or 10 points. In some embodiments, the intrathecal administration of the recombinant US enzyme may result in the annual decline of the GCA score or BSID-III developmental quotient less than about 40%, 35%, 30%, 25%, 20%, 15%, or 10%.

In some embodiments, intrathecal administration of the recombinant US enzyme further results in improvement or stabilization of one or more adaptive functions assessed by the Scales of Independent Behavior-Revised (SIB-R). In some embodiments, intrathecal administration of the recombinant I2S enzyme further results in improvement or stabilization of one or more executive functions assessed by the Behavior Rating Inventory of Executive Function® (BRIEF®).

In some embodiments, cognitive improvement described herein is achieved after a treatment period of at least 3, 4, 5, 6, 8, 10, 12, 18, 24, 30, 36, or more months. In some embodiments, cognitive improvement described herein is achieved after a treatment period of at least 1, 2, 3, 4, 5, 6, 7, 8, 9, 10 years or longer.

In various embodiments, intrathecal administration of a recombinant I2S enzyme may be used to maintain the cognitive improvement described herein for more than 3, 4, 5, 6, 8, 10, 12 months, or 1, 2, 3, 4, 5, 6, 7, 8, 9, 10, years, or the life-time of the patient being treated.

In various embodiments, one or more cognitive, adaptive, motor, and/or executive functions may also be used as biomarkers to monitor and/or optimize the treatment. For example, the dose and/or administration interval for intrathecal and/or intravenous administration (if the intrathecal administration is used in conjunction with intravenous administration) may be adjusted (e.g., increasing or decreasing) based on the GCA, BSID-III, SIB-R, and/or BRIEF score. In some embodiments, if the GCA, BSID-III, SIB-R, and/or BRIEF score fails to improve after 4, 5, or 6 doses, the dose for intrathecal administration may be increased.

The terms, "improve," "increase" or "reduce," as used herein, indicate values that are relative to a control. In some embodiments, a suitable control is a baseline assessment or measurement, such as an assessment or measurement in the same individual prior to initiation of the treatment described herein, or an assessment or measurement in a control individual (or multiple control individuals) in the absence of the treatment described herein. A "control individual" is an individual afflicted with the same disease, who is about the same age and/or gender as the individual being treated (to ensure that the stages of the disease in the treated individual and the control individuals are comparable).

The individual (also referred to as "patient" or "subject") being treated is an individual (fetus, infant, child, adolescent, or adult human) having the disease or having the potential to develop the disease. It is contemplated begin intrathecal therapy early in the trajectory of neurodevelopmental decline may be particularly effective in treating cognitive impairment. Thus, in some embodiments, a subject being treated is at least 6 moths old, 12 months old, 18 months old, 2 years old, 2.5 years old, 3 years old, 3.5 years old, 4 years old, 4.5 years old, or 5 years old. In some embodiments, a subject being treated is younger than 5, 4.5, 4, 3.5, 3, 2.5, 2, 1.5 years old, or 12, 10, 8, 6 months old. In some embodiments, a subject being treated is younger than 12, 11, 10, 9, 8, 7, 6, 5, 4, 3, 2 or 1 month old. In some embodiments, a subject being treated is younger than 29, 28, 27, 26, 25, 24, 23, 22, 21, 20, 19, 18, 17, 16, 15, 14, 13, 12, 11, 10, 9, 8, 7, 6, 5, 4, 3, 2, 1 day(s) old. In some embodiments, the subject being treated has a GCA score or BSID-III developmental quotient less than 100, 90, 80, 70, 60, 50, 40, 30, 20, 15, 10 or not testable before the treatment. In some embodiments, the subject being treated has a GCA score or BSID-III developmental quotient declined from normal baseline less than 40%, 35%, 30%, 25%, 20%, 15%, or 10% before the treatment. In some embodiments, the subject being treated has a GCA score or BSID-III developmental quotient ranging between about 60-100 (e.g., about 60-95, 60-90, 60-85, 60-80, 60-75, 60-70, 70-100, 70-95, 70-90, 70-85, 70-80, 80-100, 80-95, 80-90) before the treatment.

The invention will be more fully understood by reference to the following examples. They should not, however, be construed as limiting the scope of the invention. All literature citations are incorporated by reference.

EXAMPLES

Example 1

Evaluation of I2S Serum and/or CSF Concentration Levels in Pediatric Subjects

The experiments presented in this example were designed to evaluate suitable models for determining predictive I2S concentration in serum and/or CSF and analyze observed vs. predicted I2S concentration in pediatric subjects following IV or IT dosing.

First, experiments were conducted to investigate various compartmental models and their respective ability to fit serum and CSF concentration data after IV and IT-L administration of I2S in human subjects. Mean concentration-time profiles of I2S following IV and IT-L administration of various doses of I2S were determined in serum and CSF using standard methods.

Figure 2:
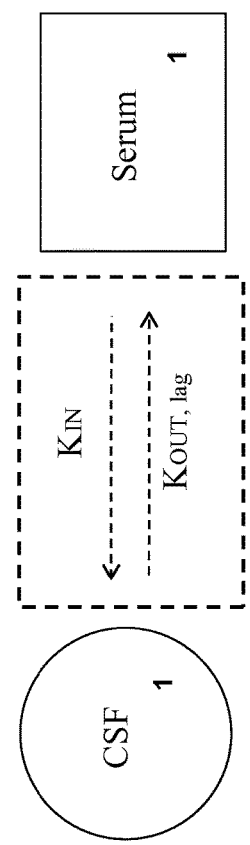
Figure 3:
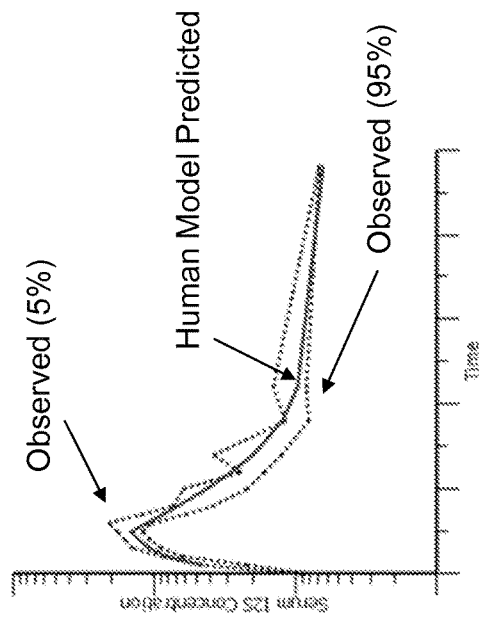
Figure 4:
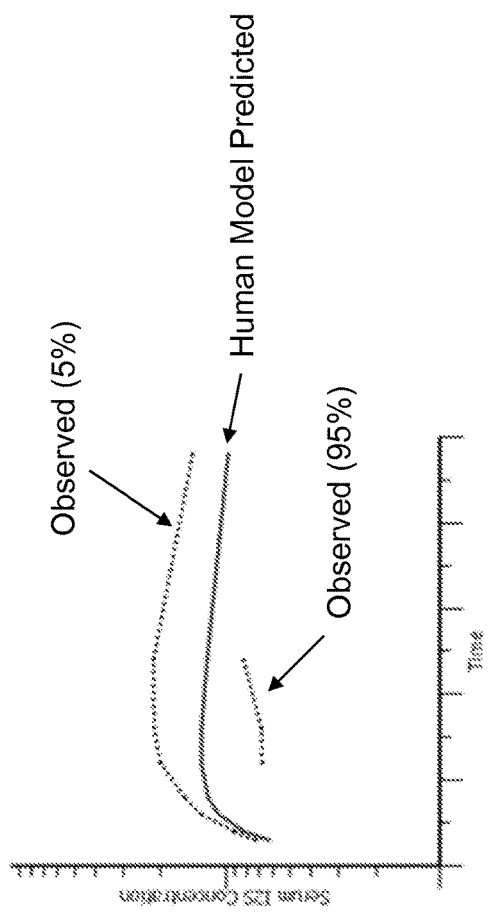

Structure modeling was used to construct a 2 compartment model (FIG. 1), as well as parameters demonstrating intercompartmental exchange between plasma and CSF (FIG. 2). Predictive analysis for both IV and IT administration was evaluated using both Human and Allometric models to estimate various I2S parameters in various matrices (e.g., serum and CSF) in children (FIGS. 3 and 4). In order to evaluate the Human model, I2S serum concentration following IV or IT administration in human patients, were analyzed using an ELISA assay. As indicated by the data, use of a Human model provides an accurate prediction of I2S serum concentration for IT and IV administration based on data from non-human primate, as compared to observed values.

However, given the difference in height, weight and body mass between humans and non-human primate subjects, additional studies were performed to evaluate use of an Allometric model. Serum concentrations levels of I2S were measured in both pediatric subjects and non-human primates over various time-points, following IT-L delivery. A correction factor was calculated based on the difference in brain to body weight ratio, for humans and non-human primates.

Figure 6:
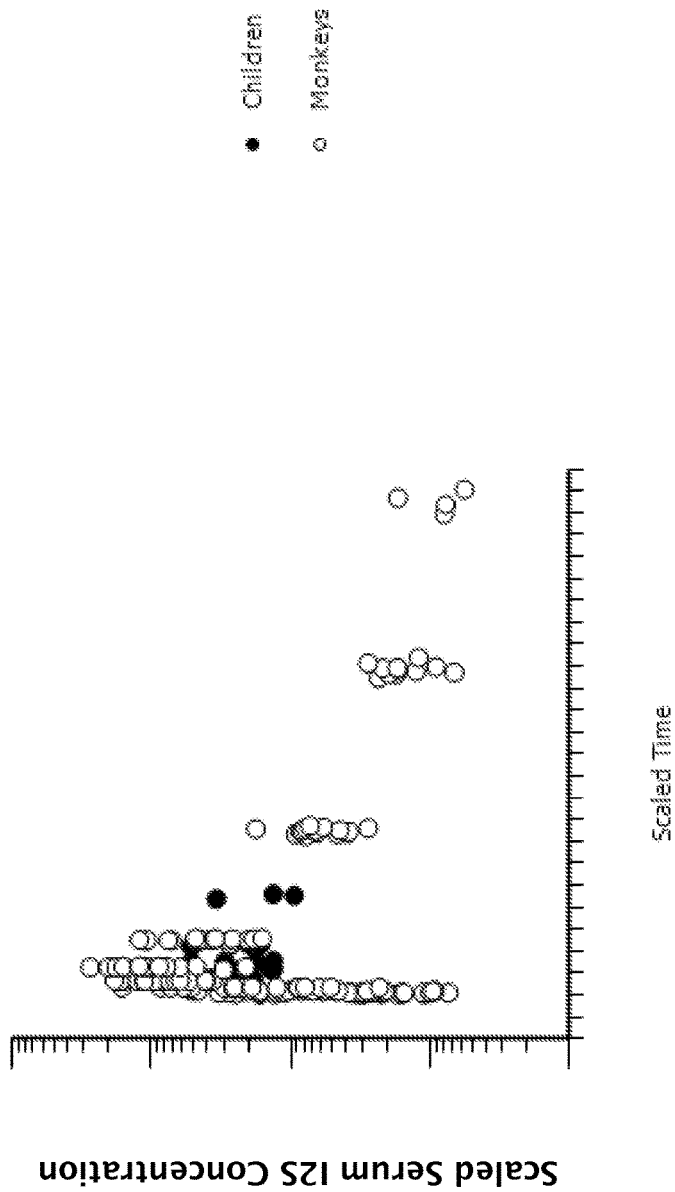
FIG. 6 illustrates exemplary body weight scaled I2S serum concentrations vs. scaled time, in both pediatric subjects and monkeys following IT-L dosing.

FIG. 5 shows allometrically scaled population pharmacokinetic (PopPK) parameters to pediatrics for IT-I2S after correction for brain/BW ratio difference between non-human primates (NHP) and children. For both serum and CSF, calculations were carried out to estimate predictive values for the various parameters within two pools of subjects: pediatric subjects less than 6 years of age and juveniles ages 6-17. Calculations were performed by taking the estimated pharmacokinetic value for each parameter in non-human primates and correcting for differences, using a brain/body weight ratio of non-human primate over child (FIG. 5). An average weight of 2.73 kg was used for non-human primates. Parameters were scaled using the median body weight (20.6 kg) of human clinical pediatric subjects (FIG. 5). FIG. 6, demonstrates an exemplary Elementary Dedrick Plot of BW-Scaled serum I2S concentration vs. scaled time in pediatric subjects and monkeys after IT-L dosing.

Figure 7:
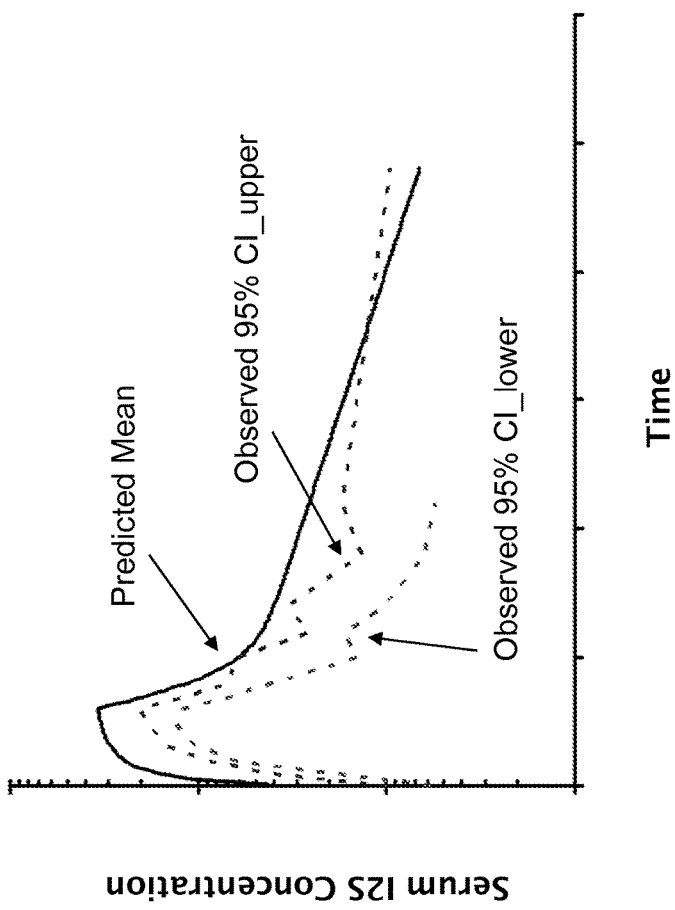
FIG. 7 illustrates the observed vs predicted serum concentration profile of I2S in pediatric subjects, following a single IV infusion.
Figure 8:
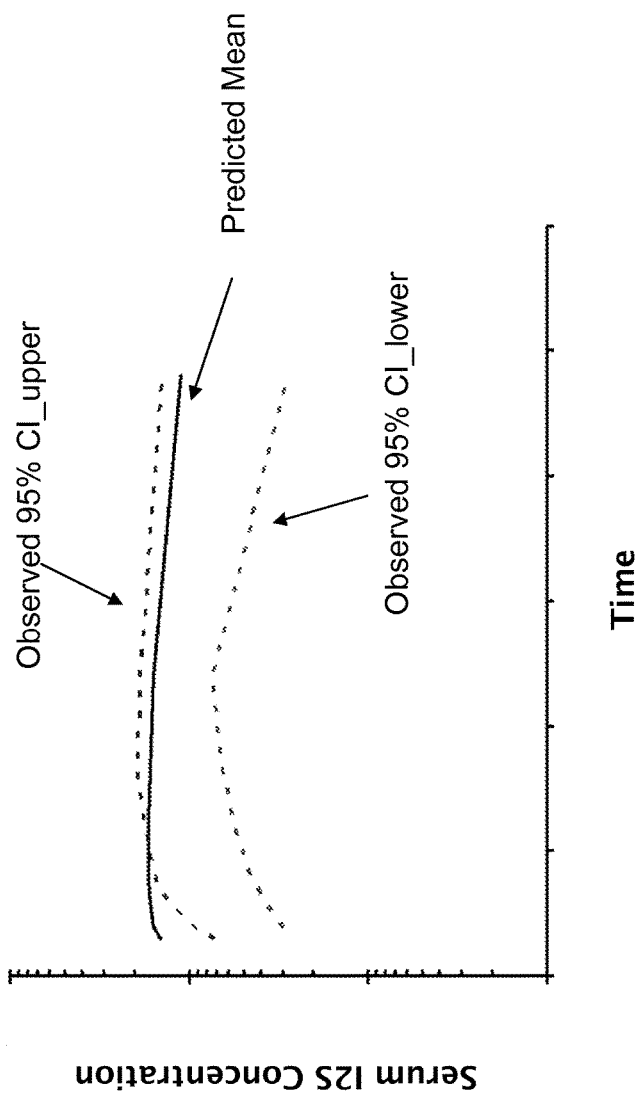
FIG. 8 illustrates the observed vs predicted serum concentration profile of I2S in pediatric subjects, following a single 10 mg IT-L administration.
Figure 9:
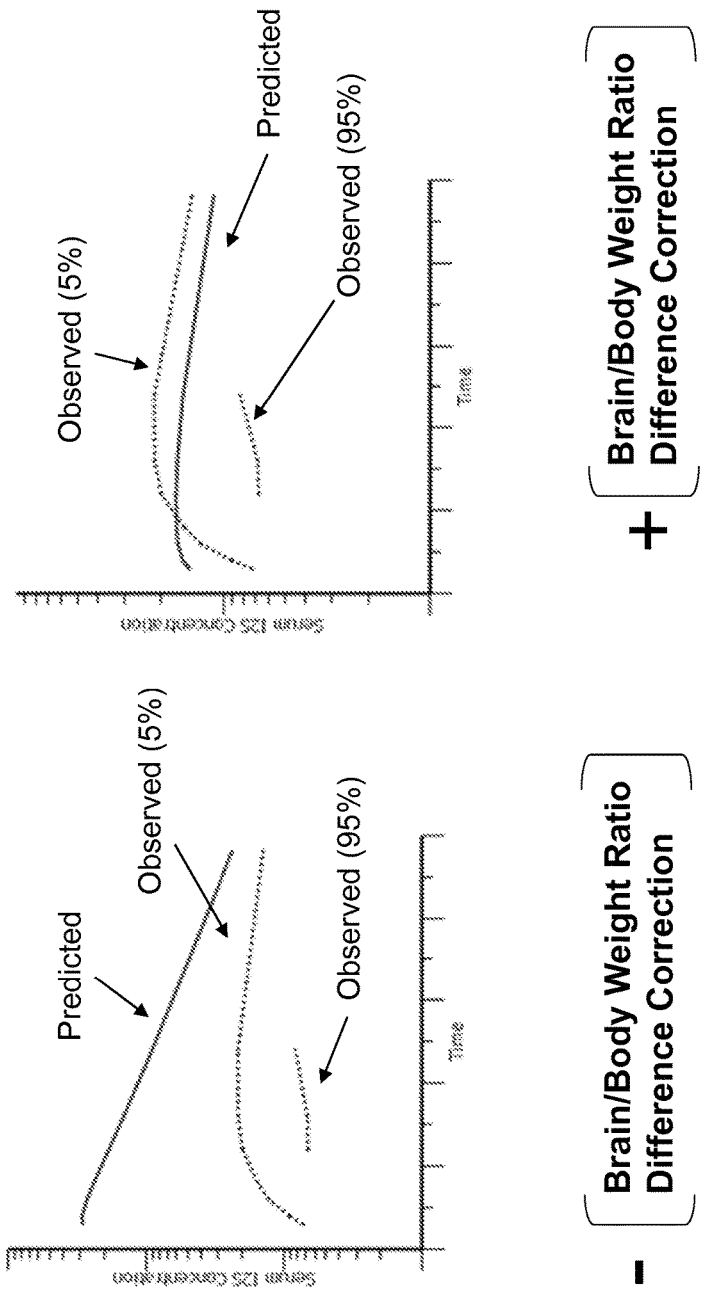
FIG. 9 illustrates the observed vs predicted serum concentration profile of I2S in pediatric subjects following, a single 10 mg IT-L administration. The exemplary concentration profile for both the observed and predicted are shown, with or without correction for brain and body weight.
Figure 10:
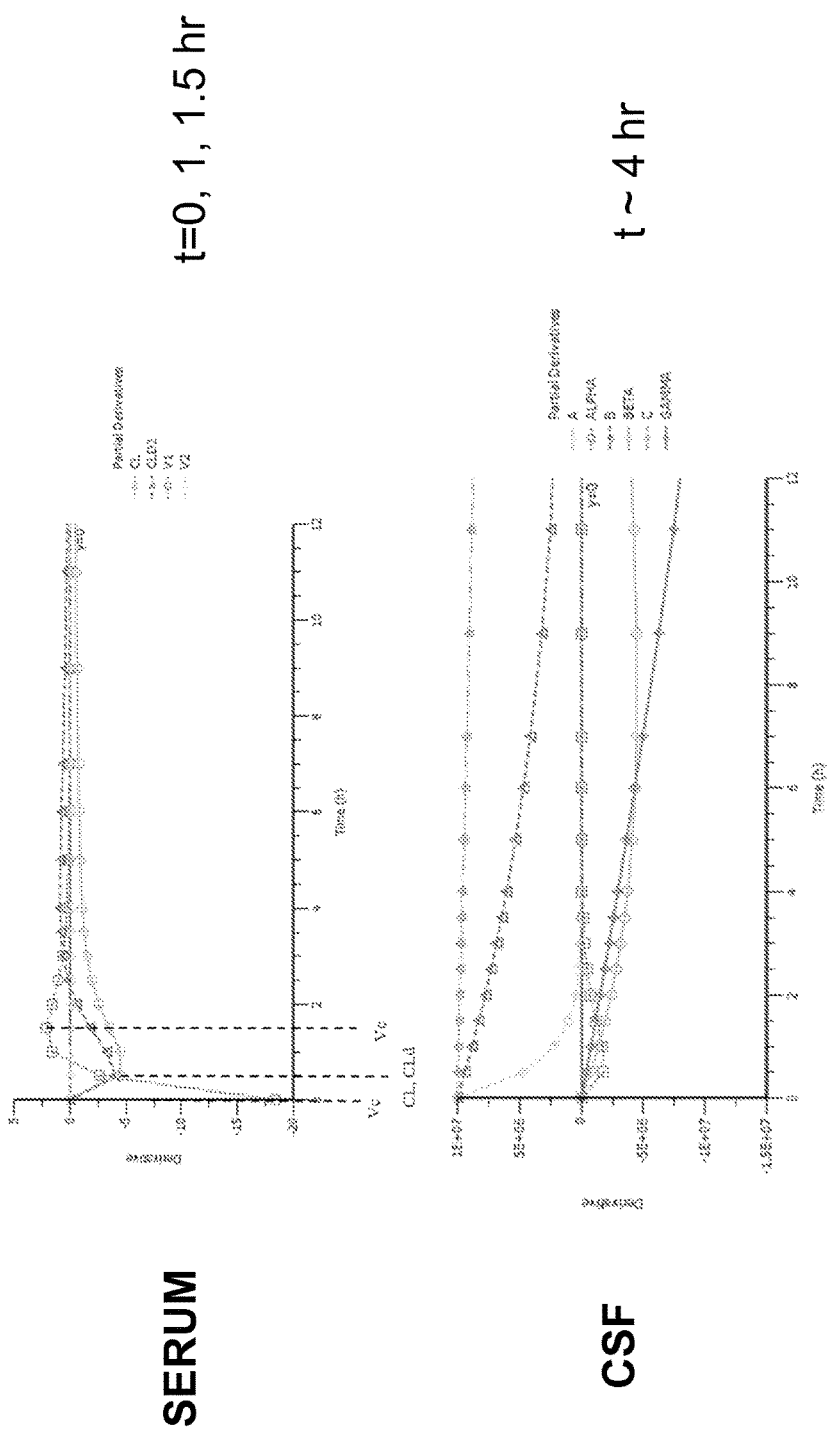
FIG. 10 illustrates I2S sampling in serum and CSF of pediatric patients over various time-points and parameters.

I2S serum concentrations obtained from pediatric subjects were analyzed and evaluated, against the predicted serum concentrations determined using the model and methods described above. FIG. 7 illustrates observed vs. predicted serum concentration—time profile of I2S in pediatric subjects following a single IV infusion of I2S at concentration of 0.5 mg/kg. The data suggests that predicted profile after IV administration was well-predicted by scaled NC model. FIG. 8 illustrates observed vs. predicted serum concentration—time profile of I2S in pediatric subjects following a single 10 mg IT-L administration. Exemplary Brain/Body weight ratio difference correction data were shown in FIG. 9. These findings show that application of Brain/BW ratio correction improves prediction. Studies were also performed to determine the optimal sampling conditions and timepoints for measuring pharmacokinetic parameters in serum and CSF following I2S delivery (FIG. 10).

These results demonstrate that the modeling approach described herein may allow accurate prediction of pharmacologic measurements in human subjects based on data obtained from non-human primates. These results also suggest that IT delivery in human subjects, in particular, pediatric subjects can impact concentration of I2S in both serum and CSF and the serum and/or CSF I2S concentrations can be used to monitor and/or optimize treatment and therapeutic efficacy.

Example 2

Figure 11:
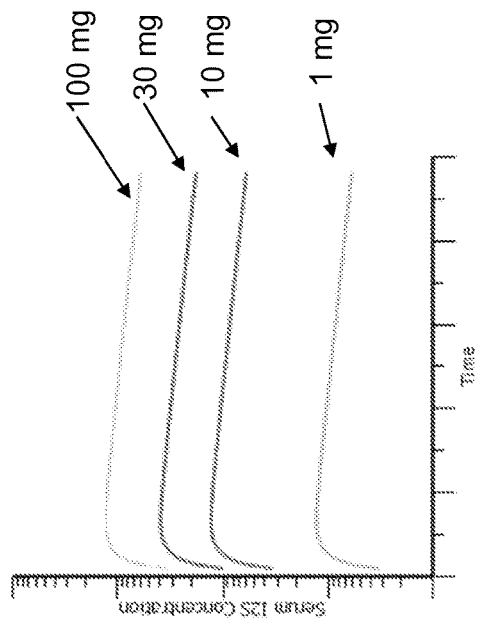
FIG. 11 illustrates the projected I2S serum concentration level in a human subject following IT administration at 1, 10, 30 and 100 mg using a Human model.
Figure 12:
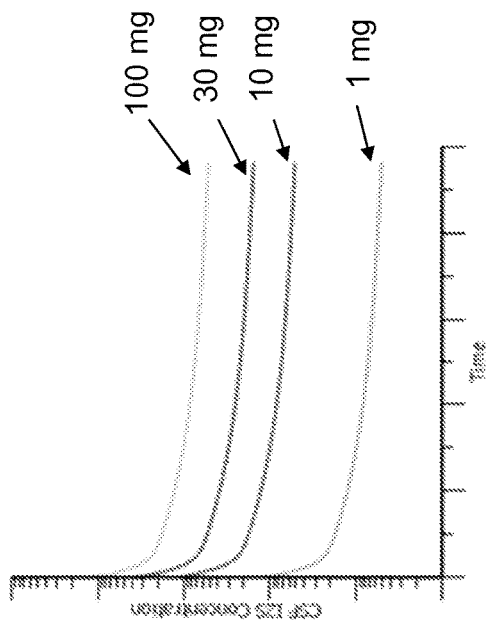
FIG. 12 illustrates the projected I2S serum concentration level in a human subject following IT administration at 1, 10, 30 and 100 mg using an Allometric model.

Evaluating Tolerance of a 100 mg Dosage and Modeling Predictive I2S Concentration in Serum and CSF Using both the experimental data and pharmacokinetic models obtained above, calculations were performed to evaluate if a monthly 100 mg dose of Idursulfase would be safe and/or offer additional efficacy beyond 30 mg dose. Using both a Human model or Allometric model, the projected plasma exposure, including projected $C_{max}$ and AUC values, anticipated after monthly 100 mg IT delivery of Idursulfase can be extrapolated (FIGS. 11 and 12). As such, the data suggests that such an approach could be used to determine the safety and efficacy of monthly 100 mg IT dose (or higher) of Idursulfase. Furthermore, it suggests that given the projected pharmacokinetic profile, a 100 mg IT dose could be effectively and safely administered to a human patient.

Example 3

Pharmacokinetic Analysis of Intrathecally Administered I2S

This serum pharmacokinetic (PK) properties of a idursulfase-IT (recombinant human I2S for intrathecal [IT] administration) were evaluated in the phase I/II clinical study designed to evaluate the safety and efficacy of IT delivery of I2S replacement enzyme in human patients with Hunter Syndrome.

Human subjects previously diagnosed with Hunters Syndrome were enrolled in the study and were drawn from a range of age groups with varying degrees of disease severity. A purified form of the lysosomal enzyme iduronate-2-sulfatase produced by recombinant DNA technology in a human cell line, was used in the clinical trials. For the study, an intrathecal drug delivery device (IDDD) was implanted in the intrathecal space surrounding the spinal chord for each subject. Depending on the study group, a monthly does of either 0, 1, 10 or 30 mg of Idursulfase was delivered intrathecally through IDDD in combination with IV administration. The monthly dosing was continued up to a period of 36 months to determine drug tolerance and efficacy. The formulation for intrathecal administration used in this study contains I2S (50 mg/ml), sodium chloride (9 mg/ml), and polysorbate 20 (0.00005 ml/ml).

To determine the pharmacokinetic profile of idursulfase in serum samples collected from pediatric patients two research arms were established. The objective of this two arm approach, was to determine the PK profile of idursulfase in serum samples collected from pediatric patients with Hunter syndrome and with cognitive impairment who received idursulfase-IT by the intrathecal route at monthly intervals in conjunction with IV administration of idursulfase (3 hr 0.5 mg/kg infusion) at weekly intervals. The initial research arm was a randomized, multicenter, multiple-dose, time-lagged, dose escalation study evaluating the safety, tolerability, and clinical activity of up to 4 dose levels of idursulfase-IT administered via an intrathecal drug delivery device (IDDD) monthly for 6-months in conjunction with weekly intravenous (IV) infusions of recombinant I2S (0.5 mg/kg) in patients with Hunter syndrome and who have cognitive impairment. Patients who completed all study requirements for the first arm were then allowed to participate in a second Interim Study, which was designed as an open-label extension of the initial study, to evaluate the long-term safety and clinical outcomes of idursulfase-IT administered in conjunction with intravenous I2S administration in pediatric patients with Hunter Syndrome and cognitive impairment.

There were four patients per treatment group enrolled in the initial research arm. An additional group of 4 patients were randomly assigned to no-IT treatment for 6-months (an IV-only-group within the IT and IV treatment groups). Patients were enrolled in Group 1 (10 mg) and Group 2 (30 mg) in a sequential, escalating fashion. Enrollment in Group 4 (1.0 mg) commenced following Group 2 enrollment. Due to the favorable PD effect observed at 30 mg, the initially planned 100 mg dose was not implemented and a 1 mg dose group was implemented instead.

The duration of idursulfase-IT treatment in the initial arm was 6 months, with patients receiving 1 dose of idursulfase-IT every 28 days. Patients who completed all study requirements in the initial arm went on to participate in an open-label extension study to evaluate the long-term safety and clinical outcomes of IT administration of idursulfase-IT.

Patients who received idursulfase-IT in the first arm received the same treatment regimen in the extension study and will continue to receive treatment for a maximum duration of 5 years.

For the initial research arm, serum pharmacokinetic analyses were performed at week 3 (following the first idursulfase-IT administration) and Week 23 (following the sixth idursulfase-IT administration). For those patients who continued on to the second arm of the study, pharmacokinetic analysis was also performed, but at month 19 and month 31. During the IT administration weeks, in both the first and second research arms, the IV dose is administered 2 days following the IT dose.

Blood Sampling

Evaluation of idursulfase concentration-time profiles from the cerebrospinal fluid (CSF) is difficult due to the limited number of clinically permissible CSF sample collections. Therefore, while determination of a comprehensive pharmacokinetic profile in CSF was not possible, idursulfase levels were evaluated indirectly by measuring systemic serum idursulfase concentration-time profiles, as sampled from the blood. Blood samples were collected from patients who received idursulfase-IT or IV at Weeks 3 and 23 (10 and 30 mg group) and Month 19 (10 mg group) and analyzed. All blood samples for PK analysis were drawn from a vessel in the arm opposite from IV infusion and placed in collection tubes without any anticoagulant and were allowed to clot at room temperature. Blood samples were collected within 15 minutes prior to idursulfase-IT administration (pre-injection baseline or Time 0) and at 0.5, 1, 1.5, 2, 3, 4, 6, 8, 12, and 24 hours following idursulfase-IT administration. Sampling times were extended to 30 and 36 hours following idursulfase-IT administration at Week 23 (30 mg group) and at Month 19. Blood samples for IV PK evaluation were collected within 15 minutes prior to IV infusion (pre-infusion baseline or Time 0), at 0.5, 1, 1.5, 2, 2.5, and 3 hours during the infusion; and at 3.5, 4, 5, 6, 7, 9, 11, and 24 hours following the initiation of IV infusion.

Analysis of Serum I2S

Serum samples for PK analysis were analyzed for idursulfase protein concentration using validated enzyme-linked immunosorbent assay (ELISA) methods. The lower limit of quantification (LLOQ) of the ELISA method used to measure serum idursulfase concentrations after IV administration was 62.5 ng/mL. The LLOQ of the assay used to measure serum idursulfase after idursulfase-IT administration was 6.25 ng/mL. A higher sensitivity idursulfase protein assay was used for the idursulfase-IT samples in order to detect and examine anticipated lower amounts of idursulfase entering systemic circulation from the CNS compartment following IT administration.

Pharmacokinetic Analysis

Pharmacokinetic parameters for idursulfase were determined by noncompartmental analysis using Phoenix Version 6.1 (Pharsight Corporation, Mountain View, Calif., USA). The actual PK blood sample collection times relative to the start of idursulfase-IT administration were used in the PK analysis. For the PK analysis of serum idursulfase concentrations after the start of IV infusion, the actual infusion times (approximately 180 min) and actual sampling times were used. Continuous data were summarized with the descriptive statistics: number of observations, mean, standard deviation (SD), geometric mean, coefficient of variation (% CV), median, minimum, and maximum values. Categorical data were summarized with frequencies and/or percentages. The pharmacokinetic parameters calculated for each sample included: maximum observed serum concentration ($C_{max}$), time of $C_{max}$ ($T_{max}$), area under the serum concentration-time curve from time zero to the last sampling time at which serum concentrations were measurable ($AUC_{0-last}$), area under the serum concentration-time curve extrapolated to infinity ($AUC_{0-\infty}$), exposure at steady state for the dosing interval ($AUC_{ss}$), terminal rate constant ($\lambda z$) derived from the slope of the log-linear regression of the log-linear terminal portion of the serum concentration-time curve, terminal half-life (t½) calculated as $0.693/\lambda z$, mean residence time extrapolated to infinity ($MRT_{inf}$); which is calculated as $AUMC_{0-\infty}/AUC_{0-\infty}$, total clearance (CL) calculated as $dose/AUC_{0-\infty}$, volume of distribution ($V_{ss}$) calculated as $MRT_{inf}\cdot CL$ and distribution of volume ($V_z$) derived from the elimination phase.

I2S-IT and IV (Week 3)

Figure 13:
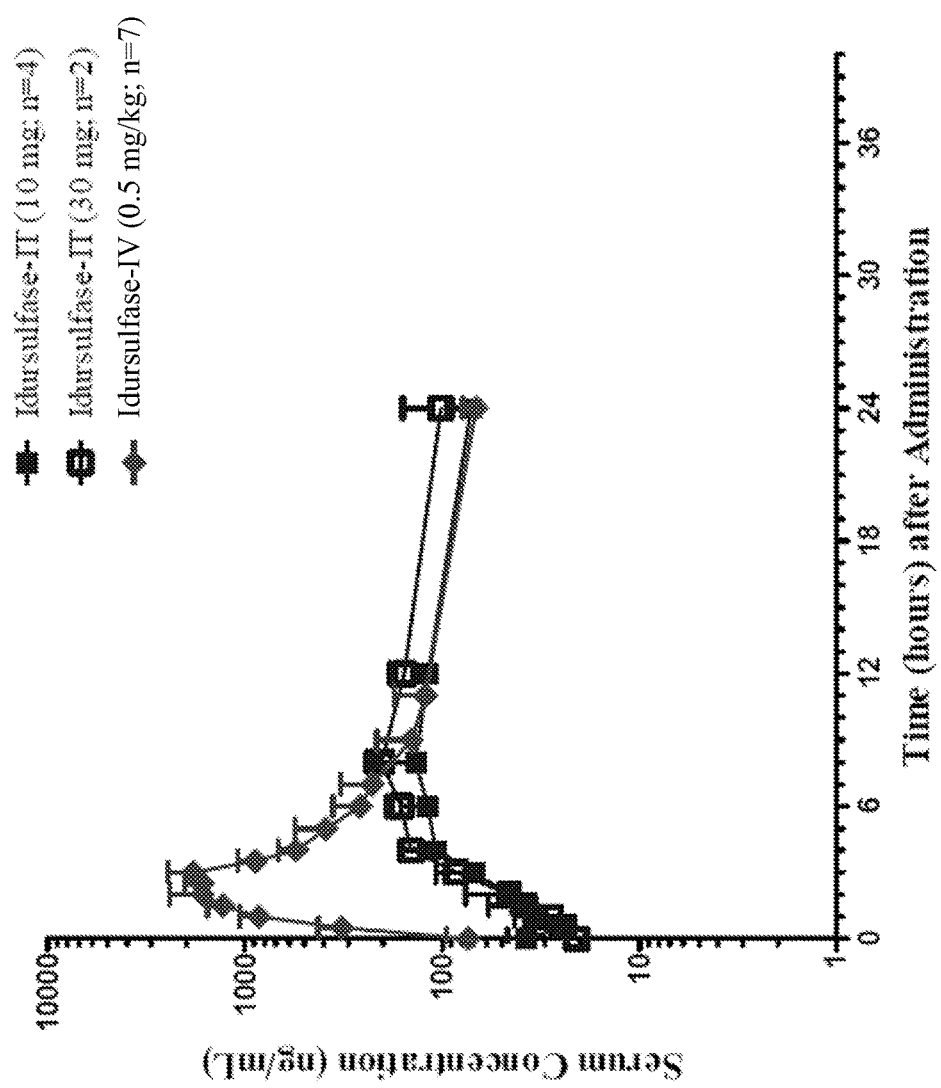
FIG. 13 demonstrates exemplary mean serum I2S concentration-time profiles of patients in the first arm at week 3.

The data demonstrates that at doses of 10 and 30 mg, idursulfase-IT exhibited similar serum idursulfase concentration-time profiles (FIG. 13). Intrathecal administration of idursulfase-IT demonstrated a slow distribution into the systemic compartment, with a maximum observed concentration ($T_{max}$) for the 10 mg and 30 mg idursulfase-IT doses of 545.5±226.1 minutes and 420±84.9 minutes, respectively. At Week 3 there was a high degree of variability in the $C_{max}$ and $AUC_{0-last}$ values of individual patients in the 10 mg (n=4) and 30 mg (n=2) idursulfase-IT groups, but in general, systemic exposure was similar for the two treatment groups. The $C_{max}$ was 144.5±65.9 ng/mL and 204.8±33 ng/mL, and the $AUC_{0-last}$ was 140084.5±45590.1 min·ng/mL and 190487.7±38569.0 min·ng/mL for the 10 and 30 mg idursulfase-IT groups, respectively (Table 5). The IV $AUC_{0-\infty}$ and $C_{max}$ for the idursulfase-IT 10 mg group at Week 3 was 469936.2±85471.3 min·ng/mL and 1695.5±376.0 ng/mL, respectively. The I2S IV $AUC_{0-\infty}$ and $C_{max}$ for the idursulfase-IT 30 mg group at Week 3 was 553300.4±190671.0 min·ng/mL and 2187.5±979.5 ng/mL, respectively (Table 8).

I2S-IT and IV (Week 23)

Figure 14:
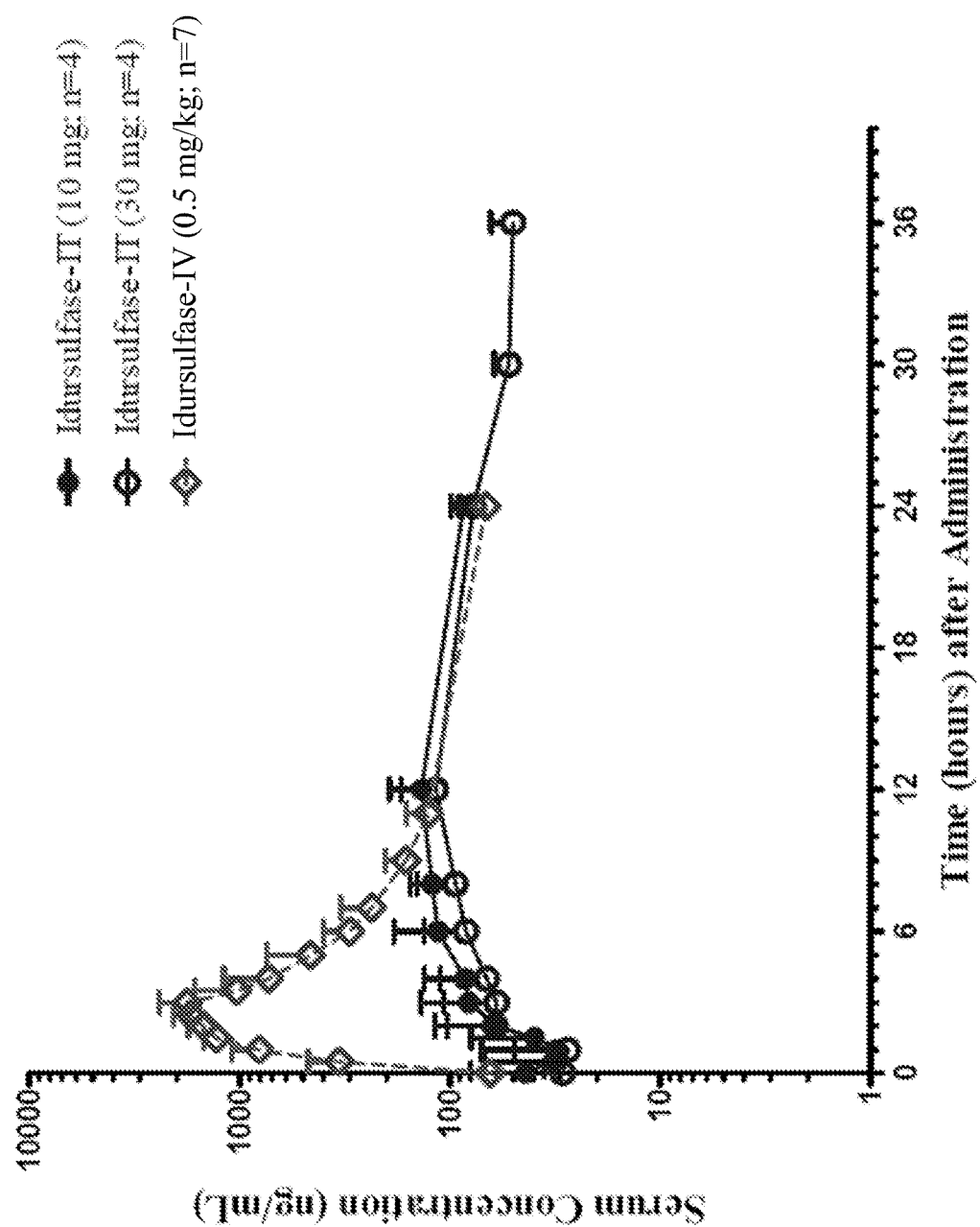
FIG. 14 demonstrates exemplary mean serum I2S concentration-time profiles of patients in the first arm at week 23.

At Week 23 the PK profiles of both idursulfase-IT dose groups were similar to Week 3 (FIG. 14). Idursulfase-IT exhibited slow distribution into the systemic compartment, with a $T_{max}$ of 570.8± 181.5 minutes and 450.5±60.3 minutes, for the 10 mg and 30 mg doses respectively. Similar to Week 3, at Week 23 there was a high degree of variability in $C_{max}$ and $AUC_{0-last}$ values of individual patients in the 10 mg (n=4) and 30 mg (n=4) idursulfase-IT groups and systemic exposure was higher for the 10 mg idursulfase-IT group. The $C_{max}$ was 150.4±50.2 ng/mL and 95.1±59.3 ng/mL, and $AUC_{0-last}$ was 150529.0± 43878.8 min·ng/mL and 102278.3± 105526.2 min·ng/mL for the 10 mg and 30 mg idursulfase-IT groups, respectively (Table 6). At Week 23, the I2S IV $AUC_{0-\infty}$ and $C_{max}$ for the idursulfase-IT 10 mg group was 483492.6±69182.3 min·ng/mL and 1704.7±410.0 ng/mL, respectively. The I2S IV $AUC_{0-\infty}$ and $C_{max}$ for the idursulfase-IT 30 mg group at Week 23 were 546934.2± 115402.7 min·ng/mL and 2142.1±660.9 ng/mL, respectively (Table 9).

I2S-IT and IV (Month 19)

Figure 15:
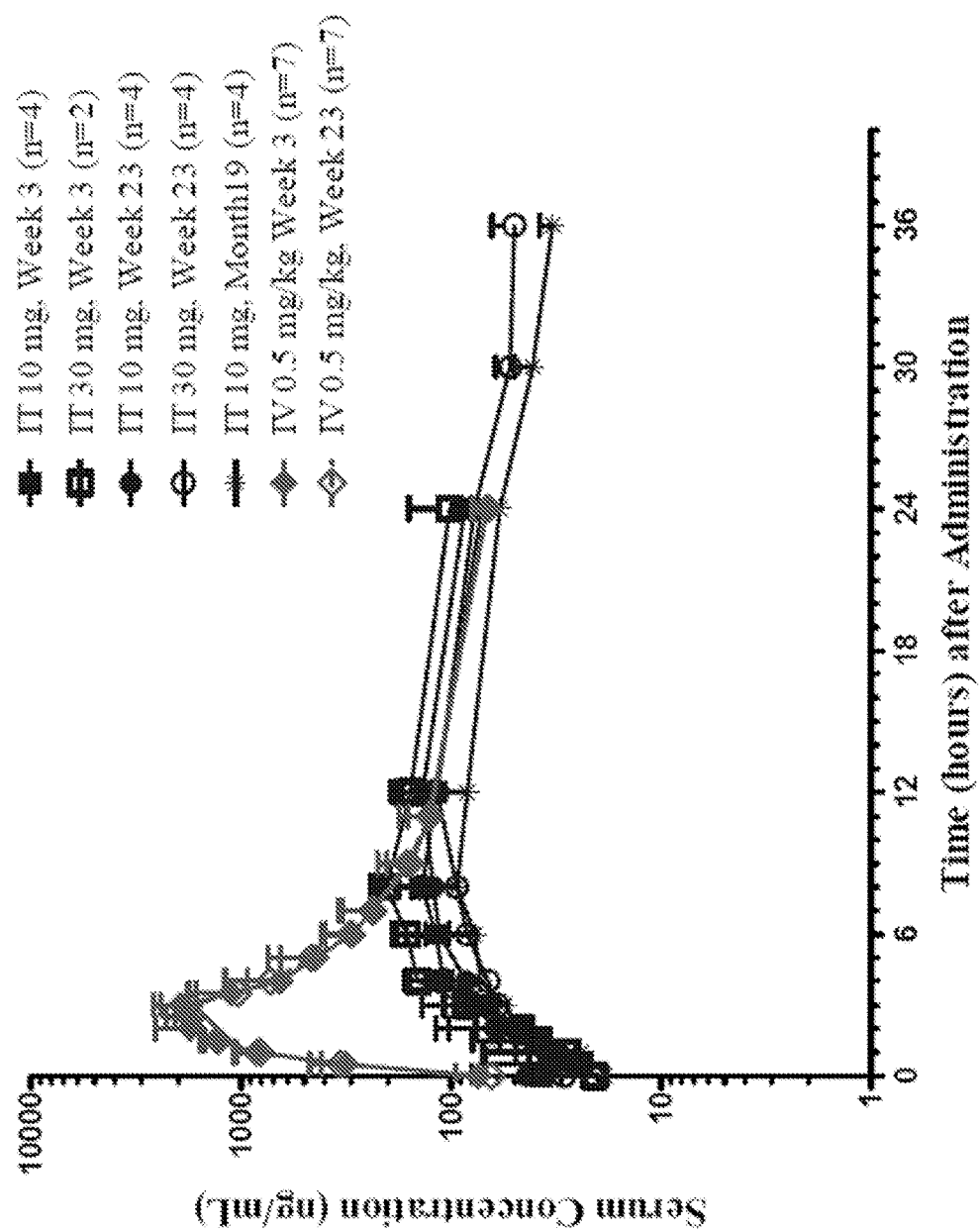
FIG. 15 demonstrates exemplary mean serum I2S concentration-time profiles of patients at week 3, week 23 and month 19.

At the Month 19 timepoint, the PK profile of idursulfase-IT is similar to that observed at Week 3 and 23 (FIG. 15). Serum concentrations of idursulfase had a $T_{max}$ of 570.0±180.0 minutes. Evaluation at Month 19 shows that the systemic exposure at the 10 mg dose of idursulfase-IT was comparable to the values observed at Week 3 and Week 23. The $C_{max}$ and $AUC_{0-last}$ were 96.4±44.3 ng/mL and 124433.3±30757.6 min·ng/mL, respectively (Table 7). Intravenously administered I2S (0.5 mg/kg) exhibited overlapping serum idursulfase concentration-time profiles (FIG. 3) as well as similar PK parameters at Week 3 and Week 23 (Table 9). At both time periods, the $C_{max}$ generally coincided with the end of infusion (3 hours).

TABLE 5

Exemplary Noncompartmental PK Parameters of Serum Idursulfase Concentrations from Patients in the First Arm Following Administration of Idursulfase-IT (Week 3)

| | $t_{1/2}$ (min) | $T_{max}$ (min) | $C_{max}$ (ng/mL) | $AUC_{0\text{-}last}$ (min · ng/mL) | $AUC_{0\text{-}x}$ (min · ng/mL) | $V_2$ (mL) | CL (mL/min) | $MRT_{inf}$ (min) |
|---|---|---|---|---|---|---|---|---|
| Patient | | | | 10 mg | | | | |
| 045-013-0004 | 1308.2 | 250.0 | 134.1 | 147351.1 | 295976.6 | 63765.4 | 33.8 | 2018.5 |
| 045-013-0005 | NC | 725.0 | 91.2 | 100284.5 | NC | NC | NC | NC |
| 045-013-0011 | NC | 720.0 | 112.9 | 111243.9 | NC | NC | NC | NC |
| 045-013-0014 | NC | 487.0 | 239.9 | 201458.4 | NC | NC | NC | NC |
| N | 1 | 4 | 4 | 4 | 1 | 1 | 1 | 1 |
| Mean | 1308.2 | 545.5 | 144.5 | 140084.5 | 295976.6 | 63765.4 | 33.8 | 2018.5 |
| SD | NC | 226.1 | 65.9 | 45590.1 | NC | NC | NC | NC |
| CV % | NC | 41.5 | 45.6 | 32.5 | NC | NC | NC | NC |
| Median | 1308.2 | 603.5 | 123.5 | 129297.5 | 295976.6 | 63765.4 | 33.8 | 2018.5 |
| Min | 1308.2 | 250.0 | 91.2 | 100284.5 | 295976.6 | 63765.4 | 33.8 | 2018.5 |
| Max | 1308.2 | 725.0 | 239.9 | 201458.4 | 295976.6 | 63765.4 | 33.8 | 2018.5 |
| $Geo_{mean}$ | 1308.2 | 502.1 | 134.9 | 134900.1 | 295976.6 | 63765.4 | 33.8 | 2018.5 |
| Patient | | | | 30 mg | | | | |
| 045-013-0003 | 622.4 | 360.0 | 181.3 | 163215.3 | 217883.3 | 123639.1 | 137.7 | 1073.6 |
| 045-013-0006 | NC | 480.0 | 228.4 | 217760.1 | NC | NC | NC | NC |
| N | 1 | 2 | 2 | 2 | 1 | 1 | 1 | 1 |
| Mean | 622.4 | 420.0 | 204.8 | 190487.7 | 217883.3 | 123639.1 | 137.7 | 1073.6 |
| SD | NC | 84.9 | 33.3 | 38569.0 | NC | NC | NC | NC |
| CV % | NC | 20.2 | 16.3 | 20.2 | NC | NC | NC | NC |
| Median | 622.4 | 420.0 | 204.8 | 190487.7 | 217883.3 | 123639.1 | 137.7 | 1073.6 |
| Min | 622.4 | 360.0 | 181.3 | 163215.3 | 217883.3 | 123639.1 | 137.7 | 1073.6 |
| Max | 622.4 | 480.0 | 228.4 | 217760.1 | 217883.3 | 123639.1 | 137.7 | 1073.6 |
| $Geo_{mean}$ | 622.4 | 415.7 | 203.5 | 188525.3 | 217883.3 | 123639.1 | 137.7 | 1073.6 |

NC—not calculated due to insufficient data points

TABLE 6

Exemplary Noncompartmental PK Parameters of Serum Idursulfase Concentrations from Patients in the First Arm Following Administration of Idursulfase-IT (Week 23)

| | $t_{1/2}$ (min) | $T_{max}$ (min) | $C_{max}$ (ng/mL) | $AUC_{0\text{-}last}$ (min · ng/mL) | $AUC_{0\text{-}x}$ (min · ng/mL) | $V_2$ (mL) | CL (mL/min) | $MRT_{inf}$ (min) |
|---|---|---|---|---|---|---|---|---|
| Patient | | | | 10 mg | | | | |
| 045-013-0004 | 1461.8 | 359.0 | 220.0 | 214132.4 | 434076.7 | 48585.1 | 23.0 | 2128.6 |
| 045-013-0005 | NC | 480.0 | 116.2 | 120864.6 | NC | NC | NC | NC |
| 045-013-0011 | NC | 724.0 | 154.1 | 145280.2 | NC | NC | NC | NC |
| 045-013-0014 | NC | 720.0 | 111.4 | 121839.0 | NC | NC | NC | NC |
| N | 1 | 4 | 4 | 4 | 1 | 1 | 1 | 1 |
| Mean | 1461.8 | 570.8 | 150.4 | 150529.0 | 434076.7 | 48585.1 | 23.0 | 2128.6 |
| SD | NC | 181.5 | 50.2 | 43878.8 | NC | NC | NC | NC |
| CV % | NC | 31.8 | 33.3 | 29.1 | NC | NC | NC | NC |
| Median | 1461.8 | 600.0 | 135.1 | 133559.6 | 434076.7 | 48585.1 | 23.0 | 2128.6 |
| Min | 1461.8 | 359.0 | 111.4 | 120864.6 | 434076.7 | 48585.1 | 23.0 | 2128.6 |
| Max | 1461.8 | 724.0 | 220.0 | 214132.4 | 434076.7 | 48585.1 | 23.0 | 2128.6 |
| $Geo_{mean}$ | 1461.8 | 547.5 | 144.7 | 146299.7 | 434076.7 | 48585.1 | 23.0 | 2128.6 |
| Patient | | | | 30 mg | | | | |
| 045-013-0003 | 656.1 | 480.0 | 182.0 | 235827.9 | 274312.5 | 103513.1 | 109.4 | 1165.9 |
| 045-013-0006 | 3898.6 | 360.0 | 75.0 | 137590.2 | 474893.4 | 355313.4 | 63.2 | 5841.3 |
| 045-014-1007 | NC | 482.0 | 48.4 | 12024.5 | NC | NC | NC | NC |
| 045-014-1009 | NC | 480.0 | 75.1 | 23670.5 | NC | NC | NC | NC |
| N | 2 | 4 | 4 | 4 | 2 | 2 | 2 | 2 |
| Mean | 2277.3 | 450.5 | 95.1 | 102278.3 | 374602.9 | 229413.2 | 86.3 | 3503.6 |
| SD | 2292.8 | 60.3 | 59.3 | 105526.2 | 141832.1 | 178049.7 | 32.7 | 3306.0 |
| CV % | 100.7 | 13.4 | 62.3 | 103.2 | 37.9 | 77.6 | 37.9 | 94.4 |
| Median | 2277.3 | 480.0 | 75.1 | 80630.3 | 374602.9 | 229413.2 | 86.3 | 3503.6 |
| Min | 656.1 | 360.0 | 48.4 | 12024.5 | 274312.5 | 103513.1 | 63.2 | 1165.9 |
| Max | 3898.6 | 482.0 | 182.0 | 235827.9 | 474893.4 | 355313.4 | 109.4 | 5841.3 |
| $Geo_{mean}$ | 1599.3 | 447.2 | 83.9 | 55127.0 | 360928.2 | 191780.1 | 83.1 | 2609.7 |

NC—not calculated due to insufficient data points

TABLE 7

Exemplary Noncompartmental PK Parameters of Serum Idursulfase Concentrations from Patients in the Second Arm Following Administration of Idursulfase-IT (Month 19)

| | $t_{1/2}$ (min) | $T_{max}$ (min) | $C_{max}$ (ng/mL) | $AUC_{0-last}$ (min · ng/mL) | $AUC_{0-x}$ (min · ng/mL) | $V_2$ (mL) | CL (mL/min) | $MRT_{inf}$ (min) |
|---|---|---|---|---|---|---|---|---|
| Patient | | | | 10 mg | | | | |
| 046-013-0004 | NC | 480.0 | 159.1 | 166524.2 | NC | NC | NC | NC |
| 046-013-0005 | 1413.3 | 360.0 | 94.6 | 119038.8 | 190710.6 | 106917.3 | 52.4 | 2183.7 |
| 046-013-0011 | 1092.2 | 720.0 | 58.8 | 92593.8 | 135247.7 | 116503.9 | 73.9 | 1860.3 |
| 046-013-0014 | 1162.1 | 720.0 | 73.1 | 119576.3 | 180115.5 | 93080.3 | 55.5 | 1969.6 |
| N | 3 | 4 | 4 | 4 | 3 | 3 | 3 | 3 |
| Mean | 1222.5 | 570.0 | 96.4 | 124433.3 | 168691.3 | 105500.5 | 60.6 | 2004.5 |
| SD | 168.9 | 180.0 | 44.3 | 30757.6 | 29443.5 | 11775.9 | 11.6 | 164.5 |
| CV % | 13.8 | 31.6 | 46.0 | 24.7 | 17.5 | 11.2 | 19.2 | 8.2 |
| Median | 1162.1 | 600.0 | 83.8 | 119307.6 | 180115.5 | 106917.3 | 55.5 | 1969.6 |
| Min | 1092.2 | 360.0 | 58.8 | 92593.8 | 135247.7 | 93080.3 | 52.4 | 1860.3 |
| Max | 1413.3 | 720.0 | 159.1 | 166524.2 | 190710.6 | 116503.9 | 73.9 | 2183.7 |
| GeoMean | 1215.0 | 547.1 | 89.7 | 121716.2 | 166859.9 | 105054.7 | 59.9 | 2000.1 |

NC—not calculated due to insufficient data points

TABLE 8

Exemplary Noncompartmental PK Parameters of Serum Idursulfase Concentrations from Patients in the First Arm Following Administration of Recombinant I2S IV (Week 3)

| | $t_{1/2}$ (min) | $T_{max}$ (min) | $C_{max}$ (ng/mL) | $AUC_{0-last}$ (min · ng/mL) | $AUC_{0-x}$ (min · ng/mL) | $V_2$ (mL) | CL (mL/min) | $MRT_{inf}$ (min) | Vss (mL/kg) |
|---|---|---|---|---|---|---|---|---|---|
| Patient | | | | Elaprase IV (0.5 mg/kg) in 10 mg idursulfase-IT dosing arm | | | | | |
| 045-013-0004 | 769.4 | 150.0 | 1211.6 | 292786.7 | 362161.9 | 1532.5 | 1.38 | 769.0 | 1061.7 |
| 045-013-0005 | 612.8 | 150.0 | 1642.8 | 415675.4 | 470928.2 | 938.6 | 1.06 | 559.2 | 593.7 |
| 045-013-0011 | 688.2 | 152.0 | 1816.7 | 413324.4 | 475376.1 | 1044.3 | 1.05 | 582.6 | 612.7 |
| 045-013-0014 | 357.5 | 180.0 | 2110.9 | 535739.4 | 571277.9 | 451.4 | 0.88 | 435.6 | 381.2 |
| N | 4 | 4 | 4 | 4 | 4 | 4 | 4 | 4 | 4 |
| Mean | 607.0 | 158.0 | 1695.5 | 414381.4 | 469936.2 | 991.7 | 1.1 | 586.6 | 662.3 |
| SD | 178.2 | 14.7 | 376.0 | 99189.8 | 85471.3 | 443.4 | 0.2 | 137.6 | 286.1 |
| CV % | 29.4 | 9.3 | 22.2 | 23.9 | 18.2 | 44.7 | 19.3 | 23.5 | 43.2 |
| Median | 650.5 | 151.0 | 1729.8 | 414499.9 | 473152.4 | 991.4 | 1.1 | 570.9 | 603.2 |
| Min | 357.5 | 150.0 | 1211.6 | 292786.7 | 362161.9 | 451.4 | 0.9 | 435.6 | 381.2 |
| Max | 769.4 | 180.0 | 2110.9 | 535739.4 | 571277.9 | 1532.5 | 1.4 | 769.0 | 1061.7 |
| Geomean | 583.6 | 157.5 | 1662.2 | 405170.2 | 463912.1 | 907.5 | 1.1 | 574.7 | 619.5 |
| Patient | | | | Elaprase IV (0.5 mg/kg) in 30 mg idursulfase-IT dosing arm | | | | | |
| 045-013-0003 | 719.7 | 180.0 | 1739.4 | 454701.0 | 519597.0 | 999.2 | 0.96 | 589.0 | 566.8 |
| 045-013-0006 | 637.9 | 120.0 | 3310.9 | 672529.5 | 758575.8 | 606.6 | 0.66 | 557.4 | 367.4 |
| 045-014-1009 | 511.4 | 182.0 | 1512.1 | 335613.3 | 381728.3 | 966.4 | 1.31 | 544.2 | 712.8 |
| N | 3 | 3 | 3 | 3 | 3 | 3 | 3 | 3 | 3 |
| Mean | 623.0 | 160.7 | 2187.5 | 487614.6 | 553300.4 | 857.4 | 1.0 | 563.6 | 549.0 |
| SD | 104.9 | 35.2 | 979.5 | 170852.6 | 190671.0 | 217.8 | 0.3 | 23.0 | 173.4 |
| CV % | 16.8 | 21.9 | 44.8 | 35.0 | 34.5 | 25.4 | 33.3 | 4.1 | 31.6 |
| Median | 637.9 | 180.0 | 1739.4 | 454701.0 | 519597.0 | 966.4 | 1.0 | 557.4 | 566.8 |
| Min | 511.4 | 120.0 | 1512.1 | 335613.3 | 381728.3 | 606.6 | 0.7 | 544.2 | 367.4 |
| Max | 719.7 | 182.0 | 3310.9 | 672529.5 | 758575.8 | 999.2 | 1.3 | 589.0 | 712.8 |
| Geomean | 616.9 | 157.8 | 2057.4 | 468193.6 | 531871.4 | 836.7 | 0.9 | 563.2 | 529.5 |

TABLE 9

Exemplary Noncompartmental PK Parameters of Serum Idursulfase Concentrations from Patients in the First Study Following Administration of Recombinant I2S IV (Week 23)

| | $t_{1/2}$ (min) | $T_{max}$ (min) | $C_{max}$ (ng/mL) | $AUC_{0-last}$ (min · ng/mL) | $AUC_{0-z}$ (min · ng/mL) | $V_2$ (mL) | CL (mL/min) | $MRT_{inf}$ (min) | $V_{ss}$ (mL/kg) |
|---|---|---|---|---|---|---|---|---|---|
| Patient | | | | Elaprase IV (0.5 mg/kg) in 10 mg idursulfase-IT dosing arm | | | | | |
| 045-013-0004 | 904.3 | 122.0 | 1448.3 | 386358.5 | 487860.2 | 1337.1 | 1.02 | 858.4 | 879.8 |
| 045-013-0005 | 848.6 | 150.0 | 1324.3 | 312708.6 | 389225.1 | 1572.7 | 1.28 | 800.2 | 1027.9 |

TABLE 9-continued

Exemplary Noncompartmental PK Parameters of Serum Idursulfase Concentrations
from Patients in the First Study Following Administration of Recombinant I2S IV (Week 23)

| | $t_{1/2}$ (min) | $T_{max}$ (min) | $C_{max}$ (ng/mL) | $AUC_{0\text{-}last}$ (min · ng/mL) | $AUC_{0\text{-}z}$ (min · ng/mL) | $V_2$ (mL) | CL (mL/min) | $MRT_{inf}$ (min) | $V_{ss}$ (mL/kg) |
|---|---|---|---|---|---|---|---|---|---|
| 045-013-0011 | 576.4 | 150.0 | 1809.5 | 449898.1 | 501870.5 | 828.5 | 1.00 | 539.8 | 537.7 |
| 045-013-0014 | 605.4 | 181.0 | 2236.5 | 500429.9 | 555014.6 | 786.8 | 0.90 | 525.2 | 473.1 |
| N | 4 | 4 | 4 | 4 | 4 | 4 | 4 | 4 | 4 |
| Mean | 733.7 | 150.8 | 1704.7 | 412348.8 | 483492.6 | 1131.3 | 1.1 | 680.9 | 729.6 |
| SD | 166.9 | 24.1 | 410.0 | 81182.7 | 69182.3 | 386.3 | 0.2 | 173.1 | 267.2 |
| CV % | 22.7 | 16.0 | 24.1 | 19.7 | 14.3 | 34.1 | 15.6 | 25.4 | 36.6 |
| Median | 727.0 | 150.0 | 1628.9 | 418128.3 | 494865.3 | 1082.8 | 1.0 | 670.0 | 708.8 |
| Min | 576.4 | 122.0 | 1324.3 | 312708.6 | 389225.1 | 786.8 | 0.9 | 525.2 | 473.1 |
| Max | 904.3 | 181.0 | 2236.5 | 500429.9 | 555014.6 | 1572.7 | 1.3 | 858.4 | 1027.9 |
| Geomean | 719.3 | 149.3 | 1669.1 | 406113.0 | 479565.7 | 1082.0 | 1.0 | 664.3 | 692.6 |
| Patient | Elaprase IV (0.5 mg/kg) in 30 mg idursulfase-IT dosing arm | | | | | | | | |
| 045-013-0003 | 1057.0 | 152.0 | 1452.7 | 330584.3 | 425895.3 | 1790.3 | 1.17 | 928.9 | 1090.5 |
| 045-013-0006 | 619.0 | 187.0 | 2770.1 | 588480.6 | 655723.4 | 680.9 | 0.76 | 531.4 | 405.2 |
| 045-014-1007 | 86.1 | 210.0 | 2203.7 | 507196.8 | 559184.0 | 111.1 | 0.89 | 226.2 | 202.3 |
| N | 3 | 3 | 3 | 3 | 3 | 3 | 3 | 3 | 3 |
| Mean | 587.4 | 183.0 | 2142.1 | 475420.6 | 546934.2 | 860.8 | 0.9 | 562.2 | 566.0 |
| SD | 486.2 | 29.2 | 660.9 | 131851.9 | 115402.7 | 853.9 | 0.2 | 352.4 | 465.5 |
| CV % | 82.8 | 16.0 | 30.9 | 27.7 | 21.1 | 99.2 | 22.3 | 62.7 | 82.2 |
| Median | 619.0 | 187.0 | 2203.7 | 507196.8 | 559184.0 | 680.9 | 0.9 | 531.4 | 405.2 |
| Min | 86.1 | 152.0 | 1452.7 | 330584.3 | 425895.3 | 111.1 | 0.8 | 226.2 | 202.3 |
| Max | 1057.0 | 210.0 | 2770.1 | 588480.6 | 655723.4 | 1790.3 | 1.2 | 928.9 | 1090.5 |
| Geomean | 383.3 | 181.4 | 2069.8 | 462094.0 | 538508.8 | 513.5 | 0.9 | 481.5 | 447.1 |

Bioavailability of Idursulfase-IT Following IT Administration

The systemic bioavailability of idursulfase-IT after intrathecal administration was calculated on a subset of patients who had measurable $AUC_{0\text{-}\infty}$ values (n=6; Table 10). A high degree of inter-patient variability was observed across the 10 and 30 mg idursulfase-IT dose groups. The mean percent bioavailability for the 10 mg and 30 mg idursulfase-IT groups was 53.2 (range of 29.9 to 88.0%) and 38.4 (range of 24.4 to 59.2%), respectively. The average bioavailability of idursulfase-IT across both dose groups was 47.7 f 20.8%.

Thus, following the 10 and 30 mg IT doses, serum concentrations of idursulfase increased slowly, indicating there was little or no leakage of the intrathecally injected idursulfase and no direct distribution into systemic circulation. Without wishing to be bound by a particular study, one possible mechanism is that idursulfase is removed from the CSF through the arachnoid villi. Materials transverse the villi by micro-pinocytosis, which is a unidirectional process mediating transport from the CSF to the venous system or the epidural space.

The finds also suggest, that during the first (Weeks 0-23) arm of the study, the 10 mg and 30 mg doses of idursulfase-IT at Week 3 and Week 23 exhibited nearly overlapping serum idursulfase concentration-time profiles. The average systemic bioavailability of idursulfase-IT following IT doses of 10 and 30 mg was approximately 48% (range 24-88%). Dose proportionality of serum idursulfase exposure was not observed between these two idursulfase doses, with respect to $C_{max}$ or $AUC_{0\text{-}last}$, suggesting that saturation of the transfer mechanism(s) from the CNS to the systemic compartment is achieved at an IT dose less than or equal to 10 mg.

Safely Profile

Nine of the 12 treated patients (3 of 4 patients in each IT dose group) reported at least one adverse event that was assessed as related to idursulfase-IT. However, no serious adverse events were considered related to idursulfase-IT. There were no deaths during the study, and no patient experienced a life-threatening adverse event or discontinued due to an adverse event. Taken together, the clinical data confirms that IT administration of recombinant I2S enzyme was safe and well tolerated.

Example 4

Intrathecal Administration of Recombinant I2S Reduces GAG Levels in Cerebrospinal Fluid MPSII (Hunter Syndrome), in its severe form, is characterized by the increase in the accumulation of GAG within the tissues of the body. Diagnosis of Hunter syndrome is correlated with the onset of progressive developmental delays, especially in adolescent patients. A Phase I/III safety trial of intrathecal enzyme replacement with idursulfase-IT using a formulation of idursulfase, has recently been completed for patients diagnosed with Hunter syndrome and suffering from sever cognitive impairment. As described in Example 3, sixteen children with MPSII and cognitive impairment were enrolled in 4 dose groups (no treatment, 1 mg, 10 mg, 30 mg). Idursulfase-IT was administered monthly for 6 consecutive months as a slow bolus via an intrathecal drug delivery device or via lumbar puncture, in conjunction with weekly intravenous infusion (0.5 mg/kg). Idursulfase-IT was generally well tolerated. There were no signs of meningeal inflammation due to contact with idursulfase-IT.

Figure 16:
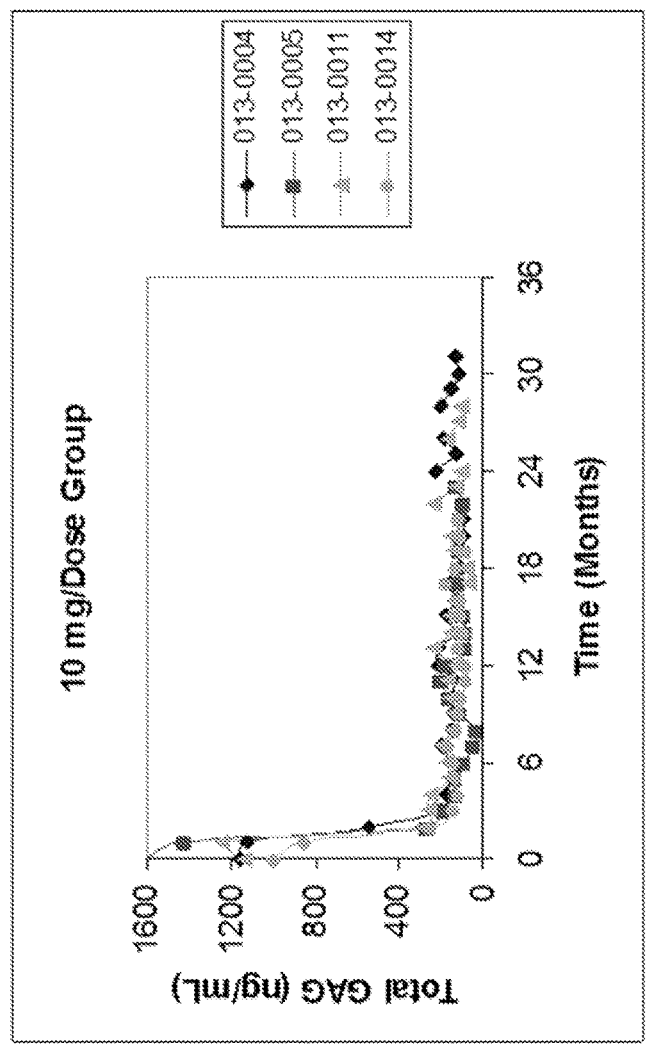
FIG. 16 describes exemplary cerebrospinal fluid levels of GAG in patients treated with 10 mg of IT recombinant I2S over a 36 month period.
Figure 17:
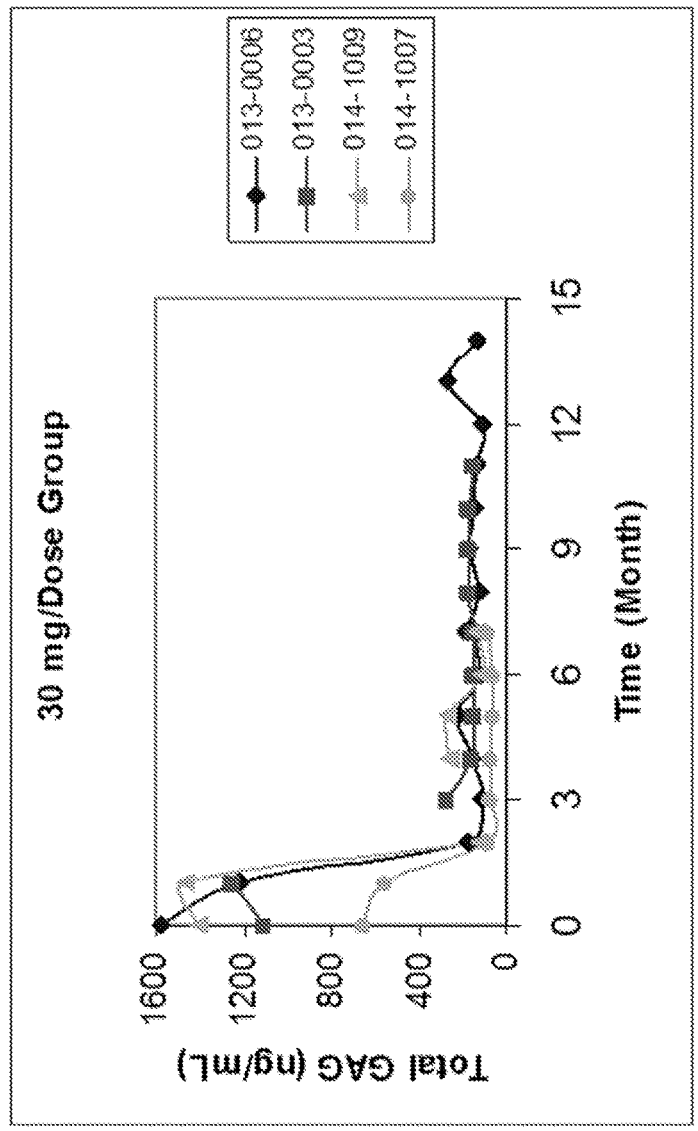
FIG. 17 describes exemplary cerebrospinal fluid levels of GAG in patients treated with 30 mg of IT recombinant I2S over a 15 month period.
Figure 18:
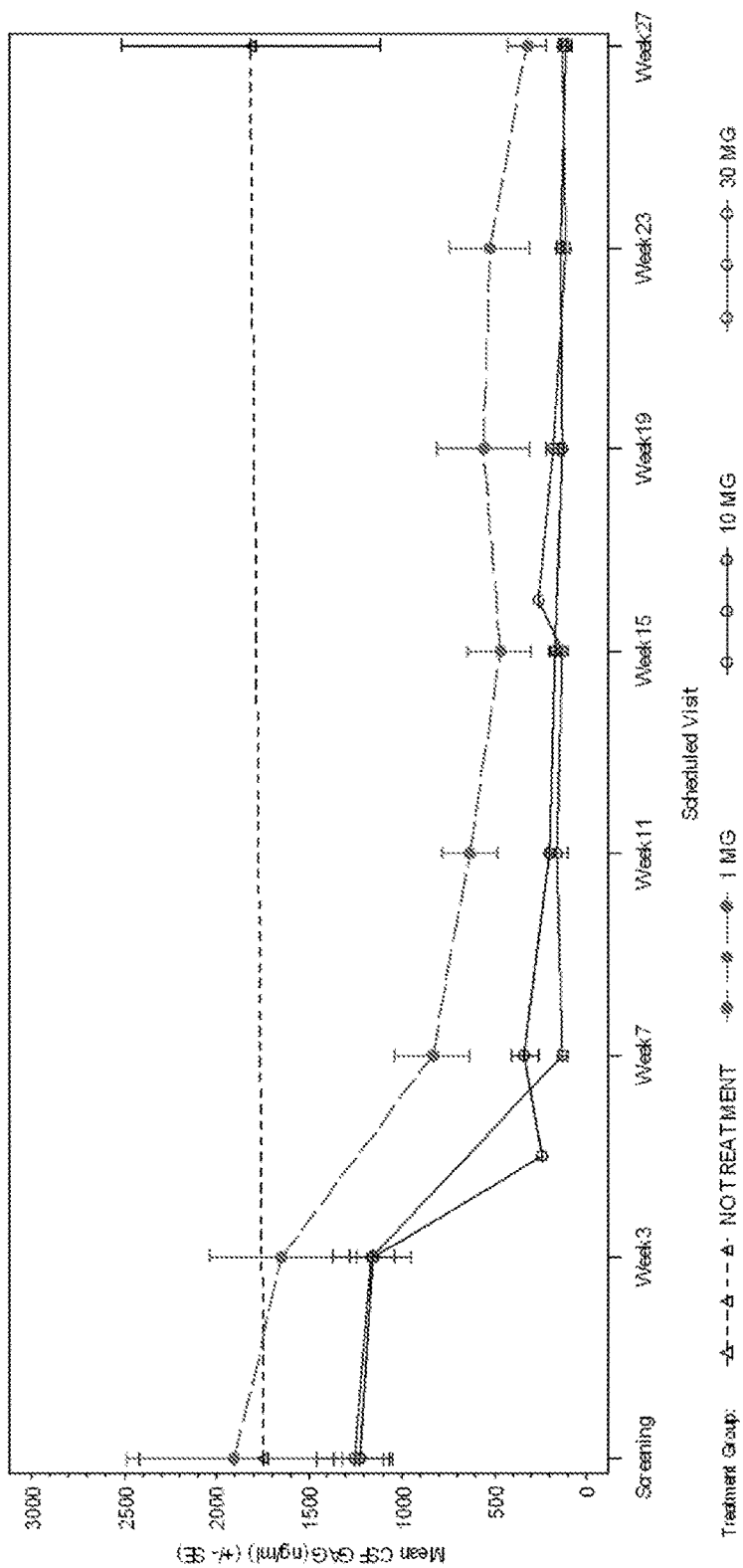
FIG. 18 demonstrates exemplary cerebrospinal fluid levels of GAG in clinical trial patients treated with 1, 10 or 30 mg of I2S over 27 weeks, as compared to control.

The levels of glycosaminoglycans (GAGs) in the cerebrospinal fluid (CSF) were measure using an enzymatic assay. GAG levels were measured during screening, during implant surgery, at every monthly dose administration, and at the end of the study. As demonstrated in FIGS. 16-18, prior to the start of enzyme replacement therapy, all patients had CSF GAG levels that were significantly elevated over the levels seen in healthy young adult volunteers or pediatric controls. In the untreated patients, the levels remained stable over a 6 month period. Administration of idursulfase-IT induced a reduction of CSF GAG levels in all treated patients (FIGS. 16-18). Furthermore, the findings suggest that stable I2S levels were typically reached after 2 or 3 injections for the 10 and 30 mg idursulfase-IT treatment (FIG. 19). No rebound of CSF GAG levels was observed when a dose was missed (Data not shown).

These data indicate that idursulfase-IT was pharmacodynamically active when administered into the CSF of children with MPSII and can effectively reduce the GAG levels in CSF.

Example 5

Intrathecal Administration of Recombinant I2S Improves Cognitive Performance

This example demonstrates that intrathecal administration of recombinant I2S enzyme improves cognitive performance in patients diagnosed with Hunter syndrome and suffering from severe cognitive impairment based on the data from a Phase I/II safety trial of intrathecal enzyme replacement with idursulfase-IT (see Example 3).

Intravenous Enzyme Replacement Therapy with recombinant idursulfase is not expected to affect the cognitive impairment due to the impenetrability of the blood-brain barrier to large proteins. For the study, 4 patients each received 1, 10 or 30 mg idursulfase-IT monthly, with exposures between 6 to 35 months, and 4 additional children received no-treatment for 6 months and then were switched to active therapy. Drug was administered via an intrathecal drug delivery device or via lumbar puncture. Of the 16 patients, the majority had advanced neurodegenerative disease at enrollment, rendering detailed cognitive and functional assessments impossible. No Serious Adverse Events related to idursulfase-IT have been observed to date.
General Conceptual Ability (GCA) Assessed by DAS-II Neurodevelopmental testing of children with MPS II typically shows normal results for the first 2 to 3 years of life; however, at around 3 to 4 years of age, those children who will manifest a developmental delay start to deviate from the normal developmental trajectory and decline rapidly over the course of a few years, generally between the ages of 3 to 9 years. The sponsor has collected longitudinal data using the DAS-II, in the absence of treatment with idursulfase-IT, in MPS II patients with evidence of cognitive impairment. These data were collected in a non-interventional screening study in MPS II patients, and in the period prior to treatment in this first-in-human study. The data suggest an annual decline of 13 to 14 points in the General Conceptual Ability (GCA) of patients. The GCA score has an average of 100 points and a standard deviation of 15 points in healthy children; therefore, an annual decline of 13 to 14 points represents a serious deterioration. These data are aligned with other prospectively collected data in the published literature.

In this Phase I/II study, the clinical activity of intrathecally administered idursulfase-IT, in conjunction with IV therapy, on patient neurodevelopmental status was assessed over 6 months using standardized measures of cognitive, adaptive, motor, and executive function appropriate for use in children with Hunter syndrome. After completion of baseline assessments, 7 of 12 patients treated with idursulfase-IT were not capable of being tested serially using the DAS-II instrument to measure their neurocognitive function over time. That these patients lacked sufficient neurocognitive function to complete serial assessments was due largely to the study inclusion criteria allowing for enrollment of severely affected patients with established neurocognitive impairment, and was a consequence of the study being designed primarily for the evaluation of safety, rather than efficacy. Of the 4 patients in the no-treatment arm, 3 patients were not testable using the DAS-II at the end of 6 months, and the assessor was not available at the end-of-study visit for testing of 1 of the untreated patients.

Longitudinal assessments using the Differential Abilities Test $2^{nd}$ version (DAS-II) were obtained in 5 patients, with follow-up times varying from 6 months to 24 months. Four of these patients, who received 10 or 30 mg idursulfase-IT, showed a stable or higher General Conceptual Ability standard score of the DAS-II. In particular, one child with a family history of severe Hunter syndrome maintained his score for up to 2 years after initiation of intrathecal enzyme replacement therapy.

A summary of exemplary results of neurocognitive testing is presented in Table 10. The data include both the General Conceptual Ability (GCA) score, as measured by the DAS-II and the Developmental Quotient (DQ), as measured by the BSID-III. The main cognitive test utilized during the study was the DAS-II; the BSID-III was a fallback measure for use in more severely affected children. Each cognitive assessment initiated with an attempt to perform the DAS-II, however, if the child failed even the simplest questions of the DAS-II, the BSID was used as an alternative.

As shown in Table 10, of the 5 patients who could be assessed serially by the DAS-II, 3 showed evidence of stabilization of neurocognitive ability after 6 months of treatment with idursulfase-IT at the 10 mg or 30 mg doses. A fourth patient (at 10 mg) showed varying results during the study, and the fifth patient who had received 1 mg, did experience a cognitive decline during the 6 months duration of the study.

TABLE 10

Summary of Neurocognitive Test Results (DAS-II GCA or BSID-III DQ)

| Patient Number | Dose | Baseline[a] | Week 3[b] | Week 15 | Week 27 | Examiner Comments |
|---|---|---|---|---|---|---|
| 045-013-0004 | 10 mg | MD | 74 | 63 | 79 | DAS-II |
| 045-013-0011 | 10 mg | 47 | 33 | 41 | 36 | DAS-II Hard to test |
| 045-013-0005 | 10 mg | 46 | MD | MD | MD | DAS-II Not testable |
| 045-013-0014 | 10 mg | 70 | 69 | 79 | 76 | DAS-II Stabilized, doing well |
| 045-013-0006 | 30 mg | 41 | MD | MD | MD | DAS-II Not testable |

TABLE 10-continued

Summary of Neurocognitive Test Results (DAS-II GCA or BSID-III DQ)

| Patient Number | Dose | Baseline[a] | Week 3[b] | Week 15 | Week 27 | Examiner Comments |
|---|---|---|---|---|---|---|
| 045-013-0003 | 30 mg | 59 | 63 | 54 | 62 | DAS-II Stabilization after documented decline |
| 045-014-1009 | 30 mg | 43 (DQ) | 40 (DQ) | MD | 44 (DQ) | BSID-III |
| 045-014-1007 | 30 mg | 22 (DQ) | 13 (DQ) | 19 (DQ) | MD | BSID-III |
| 045-013-0017 | 1 mg | 66 | 50 | 45 | 41 | DAS-II Severely affected |
| 045-014-1008 | 1 mg | 47 (DQ) | 49 (DQ) | 46 (DQ) | 43 (DQ) | BSID-III |
| 045-014-1006 | 1 mg | 16 (DQ) | 15 (DQ) | MD | 12 (DQ) | BSID-III |
| 045-013-0024 | 1 mg | MD | MD | MD | MD | Not testable |
| 045-013-0007 | No treatment | 49 | MD | NA | MD | Not testable |
| 045-013-0019 | No treatment | 34 | 32 | NA | MD | Assessor not available at the end-of-study visit |
| 045-013-0021 | No treatment | MD | MD | NA | MD | Not testable |
| 045-014-1001 | No treatment | 19 | MD | NA | MD | Not testable |

[a]Baseline is the closest screening measurement before the randomization date.
[b]For treated patients, the assessment was performed after the device had been implanted, but prior to first idursulfase-IT dose.
Abbreviations:
DQ = developmental quotient;
MD = missing data, either test was not attempted or child could not cooperate;
NA = Not Applicable.

Several children in the study could not undergo cognitive assessment at all, or could only be assessed using the BSID-III (Table 10).

Several patients also showed evidence of stabilization or improvement in adaptive (assessed using the SIB-R instrument) and executive function (assessed using the BRIEF) behaviors after receiving 6 months of treatment with idursulfase-IT.

It is expected that a clearer demonstration of clinical benefit of intrathecal idursulfase-IT therapy on preservation of neurodevelopmental function may be more evident with longer duration of treatment in patients who begin IT therapy early in the trajectory of neurodevelopmental decline.

Broad Independence Assessed by SIB-R

An assessment of Broad Independence (BI) was measured over time using the Scale of Independent Behavior-Revised (SIB-R). The Broad Independence Score is derived like an IQ score, with a population average of 100 and a standard deviation of 15. Exemplary results are shown in Table 11. After treatment, an improvement in Broad Independence Scores was noted in several patients.

Individual patient plots by chronological age of other subdomains of adaptive behaviors comprising the SIB-R (e.g., motor skills, social interaction/communication skills, personal living skills, community living skills) were generally similar to that of broad independence skills (data not shown).

TABLE 11

Summary of Neurodevelopmental Test Results (SIB-R BI)

| Patient number | Dose | Baseline[a] | Week 3[b] | Week 15 | Week 27 | Examiner Comments |
|---|---|---|---|---|---|---|
| 045-013-0004 | 10 mg | 68 | 77 | MD | 93 | |
| 045-013-0011 | 10 mg | 52 | 24 | 24 | 18 | |
| 045-013-0005 | 10 mg | 38 | 54 | 33 | 30 | |
| 045-013-0014 | 10 mg | 58 | 54 | 70 | 70 | |
| 045-013-0006 | 30 mg | 29 | 18 | 21 | 13 | |
| 045-013-0003 | 30 mg | 53 | 53 | 50 | 50 | |
| 045-014-1009 | 30 mg | 17 | 17 | MD | 23 | |
| 045-014-1007 | 30 mg | 14 | ND | ND | 1 | |
| 045-013-0017 | 1 mg | 56 | 59 | MD | 44 | |
| 045-014-1008 | 1 mg | 61 | 63 | 52 | 52 | |
| 045-014-1006 | 1 mg | 11 | 14 | ND | 14 | |
| 045-013-0024 | 1 mg | 40 | MD | 15 | ND | |
| 045-013-0007 | No treatment | MD | MD | NA | MD | Patient cognitive limitations |
| 045-013-0019 | No treatment | MD | 34 | NA | 32 | |
| 045-013-0021 | No treatment | ND | ND | NA | ND | |

TABLE 11-continued

Summary of Neurodevelopmental Test Results (SIB-R BI)

| Patient number | Dose | Baseline[a] | Week 3[b] | Week 15 | Week 27 | Examiner Comments |
|---|---|---|---|---|---|---|
| 045-014-1001 | No treatment | MD | MD | NA | MD | |

[a]Baseline is the closest screening measurement before the randomization date.
[b]For treated patients, the assessment was performed after the device had been implanted, but prior to first idursulfase-IT dose.
Abbreviations:
BI = broad independence;
MD = missing data, either test was not attempted or child could not cooperate;
NA = not applicable;
ND = number not derivable To understand whether there was a relationship between the cognitive changes and the behavioral aspects of daily living, the correlation coefficients were calculated between the DAS-II General Conceptual Ability and the overall Broad Independence Score of the SIB-R, as well as the subdomains (see Table 12).

TABLE 12

Summary of Correlations between Selected Cognitive Tests-ITT Population

| Parameter 1 | Parameter 2 | Correlation Coefficient |
|---|---|---|
| DAS-II GCA Standard Scores | DAS-II SNC Standard Scores | 0.9482 |
| DAS-II GCA Standard Scores | SIB-R Broad Independence Standard Scores | 0.8087 |
| DAS-II GCA Standard Scores | SIB-R Personal Living Skills Standard Scores | 0.5081 |
| DAS-II GCA Standard Scores | SIB-R Community Living Skills Standard Scores | 0.7473 |
| DAS-II GCA Standard Scores | SIB-R Social Interaction/ Communication Skills Standard Scores | 0.7060 |
| DAS-II GCA Standard Scores | SIB-R Motor Skills Standard Scores | 0.5467 |

Note:
Mixed models were utilized to account for repeated measurements.

As can be seen in Table 12, the DAS-II GCA and SIB-R BI standard scores were well correlated (r=0.8087), and good correlations were also seen between the GCA and standard scores for other SIB-R subdomains which, collectively, gauge a child's ability to function independently. These correlations also suggest that the cognitive improvements observed are more than academic in value and truly translate as a measure of improvement in the child's ability to function independently. These high correlation numbers constitute an important aspect of the validation of the DAS-II as clinically relevant measure in the MPS II population.

Taken together, these data demonstrate that intrathecal administration of recombinant I2S enzyme can effectively treat cognitive impairment in Hunter syndrome patients. It is expected that longer duration of treatment and/or early intervention in the trajectory of neurodevelopmental decline with idursulfase-IT may be particularly useful in improving cognitive performance by, e.g., stabilizing or increasing the DAS-II score in children with cognitive impairment due to Hunter Syndrome.

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A method of treating cognitive impairment associated with Hunter Syndrome comprising;

a) determining cognitive functions in a subject having Hunter Syndrome by DAS-II testing to provide a control general concept ability (GCA) score;

b) administering intrathecally to a said subject a recombinant iduronate-2-sulfatase (I2S) enzyme at a therapeutically effective dose of greater than 10 mg and an administration interval for a treatment period longer than 6 months;

c) determining cognitive functions in said subject during and/or after the treatment period by DAS-II testing to provide a treatment general concept ability score, wherein cognitive impairment is treated when cognitive impairment is improved, stabilized or reduced decline of cognitive function as measured by the comparison of the general conceptual ability (GCA) scores.

2. The method of claim 1, wherein the therapeutically effective dose, once administered regularly at the administration interval, results in serum $AUC_{ss}$ of the recombinant I2S enzyme within a range from approximately 200,000 min·ng/mL to approximately 1,000,000 min·ng/mL.

3. The method of claim 1, wherein the serum $AUC_{ss}$ of the recombinant I2S enzyme ranges from approximately 400,000 min·ng/mL to approximately 600,000 min·ng/mL.

4. The method of claim 1, wherein the therapeutically effective dose, once administered regularly at the administration interval, results in maximum serum concentration ($C_{max}$) of the recombinant I2S enzyme within a range from approximately 50 to about 300 ng/mL.

5. The method of claim 1, wherein the $C_{max}$ of the recombinant I2S enzyme ranges from approximately 80 to about 150 ng/mL.

6. The method of claim 1, wherein the administration interval is monthly.

7. The method of claim 1, wherein the intrathecal administration is through lumbar puncture.

8. The method of claim 1, wherein the intrathecal administration is through an Ommaya reservoir.

9. The method of claim 1, wherein the intrathecal administration is through intermittent or continuous access to an implanted intrathecal drug delivery device (IDDD).

10. The method of claim 9, wherein the intrathecal administration is through continuous access to the implanted IDDD for greater than about 0.5, 1.0, 1.5, or 2 hours.

11. The method of claim 1, wherein the one or more cognitive, adaptive, motor, and/or executive functions are assessed by the Differential Ability Scales-Second Edition (DAS-II).

12. The method of claim 11, wherein the DAS-II assessment is by a raw score, cluster score, standardized score, percentile age equivalent, developmental quotient, or the GCA score.

13. The method of claim 12, wherein the DAS-II assessment is by the GCA score.

14. The method of claim 13, wherein the intrathecal administration of the recombinant I2S enzyme results in improved GCA score.

15. The method of claim 14, wherein the improved GCA score is within the range of 85-105.

16. The method of claim 11, wherein the intrathecal administration of the recombinant I2S enzyme results in stabilization of the GCA score relative to the control.

17. The method of claim 16, wherein the intrathecal administration of the recombinant I2S enzyme results in stabilization of the GCA score for more than about 6 months.

18. The method of claim 11, wherein the intrathecal administration of the recombinant I2S enzyme results in the annual decline of the GCA score less than about 13, 12, 11, or 10 points.

19. The method of claim 1, further comprising determining one or more cognitive, adaptive, motor, and/or executive functions are assessed by Bayley Scales of Infant Development Version III (BSID-III).

20. The method of claim 19, wherein the subject in need of treatment has a GCA score or BSID-III developmental quotient less than 100, 90, 80, 70, 60, 50, 40, 30, 20, 15, 10 or not testable before the treatment.

21. The method of claim 19, wherein the intrathecal administration of the recombinant I2S enzyme results in improved BSID-III developmental quotient relative to the control.

22. The method of claim 21, wherein the improved BSID-III developmental quotient is within the range of 85-105.

23. The method of claim 19, wherein the intrathecal administration of the recombinant I2S enzyme results in stabilization of the BSID-III developmental quotient relative to the control.

24. The method of claim 23, wherein the intrathecal administration of the recombinant I2S enzyme results in stabilization of the BSID-III developmental quotient for more than about 6 months.

25. The method of claim 19, wherein the intrathecal administration of the recombinant I2S enzyme results in the annual decline of the BSID-III developmental quotient less than about 13, 12, 11, or 10 points.

26. The method of claim 1, further comprising determining control and treatment adaptive functions by assessment with the Scales of Independent Behavior-Revised (SIB-R).

27. The method of claim 1, further comprising determining control and treatment executive functions by assessment with the Behavior Rating Inventory of Executive Function® (BRIEF®).

28. The method of claim 1, wherein the control is indicative of the one or more cognitive, adaptive, motor, and/or executive functions in the subject before the treatment.

29. The method of claim 1, wherein the intrathecal administration is performed in conjunction with intravenous administration of the recombinant I2S enzyme.

* * * * *

UNITED STATES PATENT AND TRADEMARK OFFICE
CERTIFICATE OF CORRECTION

PATENT NO. : 9,682,129 B2  
APPLICATION NO. : 14/367864  
DATED : June 20, 2017  
INVENTOR(S) : Ann Barbier et al.

Page 1 of 1

It is certified that error appears in the above-identified patent and that said Letters Patent is hereby corrected as shown below:

In the Claims

Under Column 61, Claim 1, Line 58, the ";" after "comprising" should be replaced with a --:--

Under Column 61, Claim 1, Line 62, the "a" before "said subject" should be deleted and replaced with --to said subject--

Under Column 62, Claim 1, Line 56, the term "DAS-H" should be changed to --DAS-II--

Signed and Sealed this  
Thirty-first Day of October, 2017

Joseph Matal  
*Performing the Functions and Duties of the*  
*Under Secretary of Commerce for Intellectual Property and*  
*Director of the United States Patent and Trademark Office*